United States Patent
Yukawa et al.

(10) Patent No.: US 12,331,300 B2
(45) Date of Patent: Jun. 17, 2025

(54) RECOMBINANT OF HYDROGENOPHILUS BACTERIUM WITH ENHANCED ABILITY TO PRODUCE VALINE

(71) Applicant: Utilization of Carbon Dioxide Institute Co., Ltd., Tokyo (JP)

(72) Inventors: Hideaki Yukawa, Tokyo (JP); Naoto Ohtani, Tokyo (JP)

(73) Assignee: Utilization of Carbon Dioxide Institute Co., Ltd., Tokyo (JP)

(*) Notice: Subject to any disclaimer, the term of this patent is extended or adjusted under 35 U.S.C. 154(b) by 996 days.

(21) Appl. No.: 17/292,870

(22) PCT Filed: Dec. 12, 2018

(86) PCT No.: PCT/JP2018/045781
§ 371 (c)(1),
(2) Date: May 11, 2021

(87) PCT Pub. No.: WO2020/121462
PCT Pub. Date: Jun. 18, 2020

(65) Prior Publication Data
US 2021/0403927 A1    Dec. 30, 2021

(51) Int. Cl.
| | | |
|---|---|---|
| C12N 15/70 | (2006.01) | |
| C12N 1/20 | (2006.01) | |
| C12N 9/10 | (2006.01) | |
| C12N 15/74 | (2006.01) | |
| C12P 13/08 | (2006.01) | |

(52) U.S. Cl.
CPC .............. *C12N 15/74* (2013.01); *C12N 1/20* (2013.01); *C12N 9/1022* (2013.01); *C12P 13/08* (2013.01); *C12Y 202/01006* (2013.01)

(58) Field of Classification Search
CPC .... C07K 14/195; C12N 15/74; C12N 9/1022; C12N 1/20; C12P 13/08; C12Y 202/01006
USPC ........................................................ 435/7.6
See application file for complete search history.

(56) References Cited

U.S. PATENT DOCUMENTS

| | | |
|---|---|---|
| 2002/0037562 A1 | 3/2002 | Livshits et al. |
| 2007/0292914 A1 | 12/2007 | Patek et al. |
| 2009/0197309 A1 | 8/2009 | Sycheva et al. |
| 2014/0335574 A1 | 11/2014 | Sycheva et al. |

FOREIGN PATENT DOCUMENTS

| | | |
|---|---|---|
| CN | 104531598 A | 4/2015 |
| JP | 2001-231584 A | 8/2001 |
| JP | 2007-506407 A | 3/2007 |
| JP | 2008-099668 A | 5/2008 |
| JP | 2017-093465 A | 6/2017 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Reyrat et al., "Counterselectable markers: Untapped Tools for Bacterial Genetics and Pathogenesis," Infection and Immunity, 66 (9): :4011-4017 (1998).
Shigetomi "A Study of CO2 Fixation Utilizing Microorganisms," Journal of Mitsubishi Research Institute, (34) 82-93 (1999) (see partial English translation).
Kaplun et al., "Structure of the Regulatory Subunit of Acetohydroxyacid Synthase Isozyme III from *Escherichia coli*," Journal of Molecular Biology, 357: 951-963 (2006).
NCBI Reference Sequence: WP_119334643.1 (2018).
NCBI Reference Sequence: WP_021248046.1 (2015).
Wada et al., "Enhanced Valine Production in Corynebacterium glutamicum with Defective H+-ATPase and C-Terminal Truncated Acetohydroxyacid Synthase," Bioscience, Biotechnology, and Biochemistry, 72 (11): 2959-2965 (2008).
GenBank: BBD76653.1 (2018).
GenBank: X89856.1 (1996).
GenBank: AF012346.1 (2003).
GenBank: HM151400.1 (2011).
Bouacem et al., "Biochemical characterization of a novel thermostable chitinase from Hydrogenophilus hirschii strain KB-DZ44," International Journal of Biological Macromolecules, 106: 338-350 (2018).
Hayashi et al., "*Hydrogenophilus thermoluteolus* gen. nov., sp. nov., a thermophilic, facultatively chemolithoautotrophic, hydrogen-oxidizing bacterium," International Journal of Systematic Bacteriology, 49: 783-786 (1999).
Umeda et al., "Transmissibility of Hydrogen Oxidation (Hox) Plasmid from Alcaligenes hydrogenophilus," Journal of Fermentation and Bioengineering, 68 (3): 207-209 (1989).
GenBank: AP018558.1 (2018).
International Search Report issued in corresponding International Patent Application No. PCT/JP2018/045781 dated Mar. 19, 2019.

(Continued)

*Primary Examiner* — Robert B Mondesi
*Assistant Examiner* — Mohammad Y Meah
(74) *Attorney, Agent, or Firm* — Morgan, Lewis & Bockius LLP

(57) ABSTRACT

*Hydrogenophilus* bacterium which produces a mutant acetolactate synthase III small subunit formed of a mutant amino acid sequence having an amino acid substitution is able to effectively produce valine through use of carbon dioxide as a sole carbon source.

15 Claims, 2 Drawing Sheets
Specification includes a Sequence Listing.

(56) References Cited

OTHER PUBLICATIONS

Notice of reasons for refusal issued in corresponding Japanese Patent Application No. 2019-511507 drafted Jun. 10, 2019.
Tashiro et al., "2-Keto acids based biosynthesis pathways for renewable fuels and chemicals," Journal of Industrial Microbiology and Biotechnology, 42: 361-373 (2015).
Anonymous "Small subunit of the acetolactate synthase from Nitrosomonas communis", XP055883231 (2018).
Supplementary Partial European Search Report issued in corresponding European Patent Application No. 18942717.2 dated Feb. 18, 2022.

* cited by examiner

RECOMBINANT OF HYDROGENOPHILUS BACTERIUM WITH ENHANCED ABILITY TO PRODUCE VALINE

SEQUENCE LISTING SUBMISSION VIA EFS-WEB

A computer readable text file, entitled "SequenceListing.txt" created on May 11, 2021, with a file size of 9 kb contains the sequence listing for this application and is hereby incorporated by reference in its entirety.

TECHNICAL FIELD

The present invention relates to a recombinant *Hydrogenophilus* bacterium genetically enhanced to produce elevated amounts of valine, a method of producing valine using the recombinant, and a method of generating the recombinant.

BACKGROUND ART

Production of Chemical Products Using Microorganisms

The Paris Agreement, which was adopted in 2015, provides that global emissions of greenhouse gases should be promptly reduced. Under the Agreement, Japan set the goal of reducing her emission of greenhouse gases such as carbon dioxide and methane by 26% compared with year 2013 levels, by the year 2030.

Worldwide, the majority of the production of chemicals depends on petroleum resources, exacerbating the problem of increased greenhouse gas emissions. Accordingly, departure from petroleum dependency is a desirable strategy for the production of chemicals, and research and development of biorefineries that produce green chemicals from biomass is being earnestly carried out in various countries. However, the saccharification of biomass for use as raw materials of microbial fermentation necessitates complex processes, beside being costly.

As part of research geared towards departure from petroleum dependency, gases such as carbon dioxide, methane, and carbon monoxide have attracted attention as more sustainable carbon sources, and techniques for producing valuable chemicals and biofuels using microorganisms that utilize these gases are the subject of intense interest. In particular, carbon fixation of carbon dioxide and efficient utilization of carbon dioxide, a significant contributor to global warming, is highly anticipated.

Valine Production

Valine, which is one of the essential amino acids, is a substance that has become useful as, an ingredient of pharmaceuticals, food, or cosmetics, or as a livestock feed additive. Hitherto, valine has been produced either by fermentation or by chemical hydrolysis of proteins.

Nonetheless, the production of valine by fermentation of renewable resources involves an exceedingly large number of metabolic reaction steps, starting with the sugar that serves as raw material, when compared with fermentative production of lactic acid or ethanol. For this and other reasons such as feedback inhibition of metabolic enzymes by the valine product, resultant low productivity poses a persistent impediment to industrial-scale production of valine.

In microbial cells, valine is produced via four steps from pyruvic acid, which is an important intermediate metabolite within living cells. The core process proceeds as follows: acetolactate is produced from pyruvic acid through the catalytic action of acetolactate synthase; 2,3-dihydroxyisovaleric acid is then produced from acetolactate through the catalytic action of ketol acid reductoisomerase; 2-ketoisovaleric acid is then produced from 2,3-dihydroxyisovaleric acid through the catalytic action of dihydroxy acid dehydratase; finally, an amino group is transferred from glutamic acid to 2-ketoisovaleric acid through the catalytic action of branched-chain amino acid aminotransferase to produce valine.

Regarding the acetolactate synthase involved in biosynthesis of valine in *Escherichia coli*, there are three known isozymes, I, II, and III. Acetolactate synthase II is resistant to feedback inhibition by valine, whereas acetolactate synthase I and acetolactate synthase III are susceptible to the feedback inhibition by valine. Accordingly, in order to produce valine through use of microorganisms, it is required that an acetolactate synthase resistant to feedback inhibition by valine be produced at a high level.

The acetolactate synthase enzyme is composed of a large subunit and a small subunit. The large subunit harbors the catalytic function, whereas the small subunit retains the regulatory function. It is due to the function of the small subunit that enzymatic activity of the acetolactate synthase is sensitive to feedback inhibition by valine.

Among technologies for enhancing productivity of valine in microorganisms, technologies described in Patent Literatures 1 and 2 are given as methods involving using a mutant acetolactate synthase desensitized to feedback inhibition by valine.

In Patent Literature 1, there is disclosure of a technology for producing valine, involving using *Escherichia coli* in which a gene (ilvN gene) encoding the small subunit of acetolactate synthase I is mutated so as to be desensitized to feedback inhibition by valine.

In Patent Literature 2, there is disclosure of a technology for producing valine, involving using *Escherichia coli* in which a gene (ilvH gene) encoding the small subunit of acetolactate synthase III is mutated so as to be desensitized to feedback inhibition by valine.

However, each of the above-mentioned methods is a method for producing valine through the use of sugar as a carbon raw material, and is distinct from a method of producing valine through the use of carbon dioxide as a carbon raw material.

Modification of Genes on Genome

For example, when a gene encoding the small subunit of acetolactate synthase I or III is subjected to recombination, such as a mutation that causes desensitization to feedback inhibition by valine, a marker gene is utilized to serve as an indicator for selecting cells that have successfully undergone the recombination. An antibiotic resistance gene or the like is widely used as the marker gene. Cells having the antibiotic resistance gene introduced thereinto become capable of growing in the presence of an antibiotic, and hence the antibiotic resistance gene is used for selection of cells having the gene introduced thereinto, that is, positive selection.

However, variety of the marker genes is limited, and hence, when modification, such as deletion, insertion, or substitution, of a gene is performed at a plurality of sites (gene loci) on a genome, the marker gene needs to be recycled. After recombinants in each of which a gene locus of interest is modified have been selected through use of a positive selection marker, such as a drug resistance gene, as an indicator, when cells from which the positive selection marker has been removed can be selected from the recombinants, the positive selection marker can be used again at another gene locus. For that purpose, a method of efficiently selecting cells from which the positive selection marker has been removed is required.

In the modification of a gene on a genome, when a positive selection marker gene, such as a drug resistance gene, is inserted into the genome in order to select modified cells, expression of the inserted positive selection marker gene often influences expression of genes in its vicinity. In this case, in order to eliminate the influence of expression of the inserted positive selection marker gene, there arises a need to efficiently select cells from which only the positive selection marker gene has been deleted while maintaining a modified genotype.

For the selection of the cells from which a positive selection marker has been removed as described above, that is, counterselection, it is appropriate to use a genetic marker that, when expressed, kills cells, that is, a counterselection marker. According to this method, through use of the positive selection marker and the counterselection marker linked to each other, cells that have not been killed because of removal of the counterselection marker are selected, and thus cells from which the positive selection marker has been removed as well as the counterselection marker can be selectively acquired.

In many bacteria, including *Escherichia coli*, a levansucrase gene (sacB) derived from *Bacillus subtilis* is widely used as the counterselection marker. *Escherichia coli* having the sacB gene introduced thereinto becomes unable to grow in the presence of sucrose. Through utilization of this property, *Escherichia coli* that does not carry the sacB gene can be selectively acquired by selecting *Escherichia coli* that has grown in a medium supplemented with sucrose.

In *Escherichia coli* and the like, there is also a known counterselection method involving utilizing a streptomycin sensitivity gene.

It is known that a streptomycin-resistant strain emerges at a certain frequency even for a bacterium that is originally sensitive to streptomycin serving as an antibiotic. Such streptomycin-resistant strain has a mutation caused in a gene encoding ribosomal protein S12 (rpsL gene), and an amino acid substitution in ribosomal protein S12 resulting from the mutation serves as a cause of streptomycin resistance. In this case, the mutant rpsL gene serving as a cause of streptomycin resistance (hereinafter sometimes referred to as "rpsL*") is called a streptomycin resistance gene.

When a wild-type (naturally occurring) rpsL gene is introduced into such streptomycin-resistant strain, the host bacterium becomes streptomycin-sensitive. That is, the wild-type rpsL gene is a dominant gene over the rpsL* gene (streptomycin resistance gene), which is a mutant rpsL gene. In this case, the rpsL gene is sometimes called a streptomycin sensitivity gene.

That is, there is known a counterselection method involving acquiring a streptomycin-resistant strain of *Escherichia coli* or the like, using the streptomycin-resistant strain as a host, and using the wild-type rpsL gene (streptomycin sensitivity gene) as a counterselection marker (Non Patent Literature 1).

CITATION LIST

Patent Literatures

[Patent Literature 1] JP2001-231584A
[Patent Literature 2] JP2008-099668A

Non Patent Literatures

[Non Patent Literature 1] Counterselectable markers: untapped tools for bacterial genetics and pathogenesis. Reyrat J M, Pelicic V, Gicquel B, Rappuoli R. Infect. Immun. (1998) 66:4011-4017

SUMMARY OF INVENTION

Technical Problem

A first objective of the present invention is to provide a *Hydrogenophilus* bacterium recombinant capable of efficiently producing valine through utilization of carbon dioxide as a sole carbon source, and a method of efficiently producing valine using the recombinant.

A second objective of the present invention is to provide a method of efficiently generating a recombinant in a *Hydrogenophilus* bacterium.

The inventors of the present invention have made investigations in order to achieve the above-mentioned objectives, and have obtained the following findings.

Technology for Modifying Host Gene

A *Hydrogenophilus* bacterium is a hydrogen-oxidizing bacterium that grows by producing an organic substance from carbon dioxide through utilization of hydrogen energy. In general, hydrogen-oxidizing bacteria have extremely low growth rates. However, the *Hydrogenophilus* bacterium has a high growth rate, and has a much higher carbon fixation ability of carbon dioxide than plants and photosynthetic bacteria. The *Hydrogenophilus* bacterium produces valine, but at low productivity because a metabolic enzyme is subjected to feedback inhibition by the valine. In order to impart a valine-producing ability on an industrial scale, a gene encoding an enzyme that catalyzes a reaction for producing valine needs to have a mutation introduced thereinto to be desensitized to the feedback inhibition. However, there has been no technology for performing modification (e.g., deletion, substitution, or addition (including insertion)) of a gene on the genome of the *Hydrogenophilus* bacterium.

In this regard, the inventors of the present invention have extensively investigated techniques for genetic modification in the *Hydrogenophilus* bacterium, and have succeeded in carrying out recombination of the *Hydrogenophilus* bacterium in which a positive selection marker can be recycled, by combining a streptomycin-resistant strain of the *Hydrogenophilus* bacterium and a wild-type rpsL gene (streptomycin sensitivity gene).

That is, the inventors of the present invention have found that a streptomycin-resistant strain of the *Hydrogenophilus* bacterium can be isolated, and that the rpsL gene of the *Hydrogenophilus* bacterium can function as a streptomycin sensitivity gene for the streptomycin-resistant strain, and can be used as a counterselection marker therefor.

No positive selection marker that can be used in the *Hydrogenophilus* bacterium has hitherto been known. The inventors of the present invention have found that the introduction of a hygromycin phosphotransferase gene into the *Hydrogenophilus* bacterium imparts hygromycin resistance thereto, and hence the gene can be used as a positive selection marker. The inventors have also found that the introduction of a neomycin/kanamycin phosphotransferase gene or a kanamycin nucleotidyltransferase gene into the *Hydrogenophilus* bacterium imparts kanamycin resistance thereto, and hence the gene can be used as a positive selection marker.

A known example of a hygromycin phosphotransferase gene is the gene encoding hygromycin B phosphotransferase of *Escherichia coli* (hph) (Plasmid-encoded hygromycin B resistance: the sequence of hygromycin B phosphotransferase gene and its expression in *Escherichia coli* and *Saccharomyces cerevisiae*. Gritz L, Davies J. Gene (1983) 25: 179-188).

Known examples of genes for imparting kanamycin resistance, are the gene encoding neomycin phosphotransferase of transposon Tn5 of *Escherichia coli* (nptII) and the gene encoding kanamycin nucleotidyltransferase of *Staphylococcus aureus* (knt) (Small mobilizable multi-purpose cloning vectors derived from the *Escherichia coli* plasmids pK18 and pK19: selection of defined deletions in the chromosome of *Corynebacterium glutamicum*. Schafer A, Tauch A, Jager W, Kalinowski J, Thierbach G, Puhler A. Gene (1994) 145: 69-73; Enzymatic and nucleotide sequence studies of a kanamycin-inactivating enzyme encoded by a plasmid from thermophilic bacilli in comparison with that encoded by plasmid pUB110. Matsumura M, Katakura Y, Imanaka T, Aiba S. J. Bacteriol. (1984) 160: 413-420).

According to an investigation made by the inventors of the present invention, it was observed that, although the introduction of a heterologous gene into the *Hydrogenophilus* bacterium did not result in its expression in many cases, the hygromycin phosphotransferase gene did express a protein that functions in the *Hydrogenophilus* bacterium, and thereby impart hygromycin resistance thereto. It was also observed that the neomycin/kanamycin phosphotransferase gene and the kanamycin nucleotidyltransferase gene each expressed proteins that function in the *Hydrogenophilus* bacterium, and thereby impart kanamycin resistance thereto.

Valine Production

An ilvH gene encoding an acetolactate synthase III small subunit is present on the genome of the *Hydrogenophilus* bacterium. Acetolactate synthase III is subjected to feedback inhibition by valine, and hence, in the present invention, an attempt has been made to introduce a mutation expected to cause desensitization to feedback inhibition by valine into the gene encoding the acetolactate synthase on the genome of the *Hydrogenophilus* bacterium.

As a result, it has been found that a mutant acetolactate synthase III in which, in SEQ ID NO: 1 serving as the amino acid sequence of the acetolactate synthase III small subunit of the *Hydrogenophilus* bacterium, Asn at amino acid No. 11 is substituted by Asp, His, or Ala, Gly at amino acid No. 14 is substituted by Asp or Ala, Ser at amino acid No. 17 is substituted by Phe, Asn at amino acid No. 29 is substituted by Lys, Tyr, Asp, or His, Thr at amino acid No. 34 is substituted by Ile, Ala at amino acid No. 36 is substituted by Val, Arg at amino acid No. 84 and all subsequent amino acids are deleted, or Leu at amino acid No. 131 is substituted by Arg is desensitized to feedback inhibition by valine. That is, growth of a wild-type *Hydrogenophilus* bacterium is inhibited in the presence of 1 mM valine, but growth of a *Hydrogenophilus* bacterium having the above-mentioned mutation introduced into the gene encoding acetolactate synthase III is not inhibited even in the presence of a high concentration of valine, and accumulates valine in a culture liquid. Such a *Hydrogenophilus* bacterium recombinant produces valine more efficiently through use of carbon dioxide as a sole carbon source.

The present invention has been completed on the basis of the above-mentioned findings, and provides the following *Hydrogenophilus* bacterium recombinant, method of producing valine, method of producing a recombinant, and the like.

Item 1. A mutant acetolactate synthase III small subunit of any one of the following (1) to (3):

(1) a mutant acetolactate synthase III small subunit formed of a mutant amino acid sequence having a mutation of any one of the following (a) to (h) in an amino acid sequence set forth in SEQ ID NO: 1:
  (a) a substitution of Asn at amino acid No. 11 with Asp, His, or Ala;
  (b) a substitution of Gly at amino acid No. 14 with Asp or Ala;
  (c) a substitution of Ser at amino acid No. 17 with Phe;
  (d) a substitution of Asn at amino acid No. 29 with Lys, Tyr, Asp, or His;
  (e) a substitution of Thr at amino acid No. 34 with Ile;
  (f) a substitution of Ala at amino acid No. 36 with Val;
  (g) a deletion of Arg at amino acid No. 84 and all subsequent amino acids; and
  (h) a substitution of Leu at amino acid No. 131 with Arg;

(2) a mutant acetolactate synthase III small subunit that is formed of an amino acid sequence having 90% or more identity to the mutant amino acid sequence described in (1), and that has acetolactate synthase III small subunit activity and is suppressed in feedback inhibition by valine,
  provided that
  when the mutant amino acid sequence has the mutation of (a), the amino acid at amino acid No. 11 is Asp, His, or Ala,
  when the mutant amino acid sequence has the mutation of (b), the amino acid at amino acid No. 14 is Asp or Ala,
  when the mutant amino acid sequence has the mutation of (c), the amino acid at amino acid No. 17 is Phe,
  when the mutant amino acid sequence has the mutation of (d), the amino acid at amino acid No. 29 is Lys, Tyr, Asp, or His,
  when the mutant amino acid sequence has the mutation of (e), the amino acid at amino acid No. 34 is Ile,
  when the mutant amino acid sequence has the mutation of (f), the amino acid at amino acid No. 36 is Val,
  when the mutant amino acid sequence has the mutation of (g), the amino acid at amino acid No. 84 and all subsequent amino acids are deleted, and
  when the mutant amino acid sequence has the mutation of (h), the amino acid at amino acid No. 131 is Arg; and (3) a mutant acetolactate synthase III small subunit that is formed of an amino acid sequence having one or a plurality of amino acids deleted, substituted, or added in the mutant amino acid sequence described in (1), and that has acetolactate synthase III small subunit activity and is suppressed in feedback inhibition by valine,
  provided that
  when the mutant amino acid sequence has the mutation of (a), the amino acid at amino acid No. 11 is Asp, His, or Ala,
  when the mutant amino acid sequence has the mutation of (b), the amino acid at amino acid No. 14 is Asp or Ala,
  when the mutant amino acid sequence has the mutation of (c), the amino acid at amino acid No. 17 is Phe,
  when the mutant amino acid sequence has the mutation of (d), the amino acid at amino acid No. 29 is Lys, Tyr, Asp, or His,
  when the mutant amino acid sequence has the mutation of (e), the amino acid at amino acid No. 34 is Ile,
  when the mutant amino acid sequence has the mutation of (f), the amino acid at amino acid No. 36 is Val,
  when the mutant amino acid sequence has the mutation of (g), the amino acid at amino acid No. 84 and all subsequent amino acids are deleted, and when the mutant amino acid sequence has the mutation of (h), the amino acid at amino acid No. 131 is Arg.

Item 2. A mutant acetolactate synthase III small subunit gene of any one of the following (4) to (6):
(4) a gene formed of a mutant base sequence having a mutation of any one of the following (i) to (p) in a base sequence set forth in SEQ ID NO: 2:
  (i) a substitution of AAC at base Nos. 31 to 33 with GAT, GAC, CAT, CAC, GCT, GCC, GCA, or GCG;
  (j) a substitution of GGC at base Nos. 40 to 42 with GAT, GAC, GCT, GCC, GCA, or GCG;
  (k) a substitution of TCG at base Nos. 49 to 51 with TTT or TTC;
  (l) a substitution of AAC at base Nos. 85 to 87 with AAA, AAG, TAT, TAC, GAT, GAC, CAT, or CAC;
  (m) a substitution of ACC at base Nos. 100 to 102 with ATT, ATC, or ATA;
  (n) a substitution of GCA at base Nos. 106 to 108 with GTT, GTC, GTA, or GTG;
  (o) a substitution of CGC at base Nos. 250 to 252 with TAA, TAG, or TGA; and
  (p) a substitution of CTC at base Nos. 391 to 393 with CGT, CGC, CGA, CGG, AGA, or AGG;
(5) a gene formed of a base sequence having 90% or more identity to the mutant base sequence described in (4), the gene encoding a mutant acetolactate synthase III small subunit that has acetolactate synthase III small subunit activity and is suppressed in feedback inhibition by valine,
  provided that
    when the mutant base sequence has the mutation of (i), the bases at base Nos. 31 to 33 are GAT, GAC, CAT, CAC, GCT, GCC, GCA, or GCG,
    when the mutant base sequence has the mutation of (j), the bases at base Nos. 40 to 42 are GAT, GAC, GCT, GCC, GCA, or GCG,
    when the mutant base sequence has the mutation of (k), the bases at base Nos. 49 to 51 are TTT or TTC,
    when the mutant base sequence has the mutation of (l), the bases at base Nos. 85 to 87 are AAA, AAG, TAT, TAC, GAT, GAC, CAT, or CAC,
    when the mutant base sequence has the mutation of (m), the bases at base Nos. 100 to 102 are ATT, ATC, or ATA,
    when the mutant base sequence has the mutation of (n), the bases at base Nos. 106 to 108 are GTT, GTC, GTA, or GTG,
    when the mutant base sequence has the mutation of (o), the bases at base Nos. 250 to 252 are TAA, TAG, or TGA, and
    when the mutant base sequence has the mutation of (p), the bases at base Nos. 391 to 393 are CGT, CGC, CGA, CGG, AGA, or AGG; and
(6) a gene that hybridizes with DNA formed of a base sequence complementary to the mutant base sequence described in (4) under stringent conditions, and that encodes a mutant acetolactate synthase III small subunit having acetolactate synthase III small subunit activity and being suppressed in feedback inhibition by valine,
  provided that
    when the mutant base sequence has the mutation of (i), the bases at base Nos. 31 to 33 are GAT, GAC, CAT, CAC, GCT, GCC, GCA, or GCG,
    when the mutant base sequence has the mutation of (j), the bases at base Nos. 40 to 42 are GAT, GAC, GCT, GCC, GCA, or GCG,
    when the mutant base sequence has the mutation of (k), the bases at base Nos. 49 to 51 are TTT or TTC,
    when the mutant base sequence has the mutation of (1), the bases at base Nos. 85 to 87 are AAA, AAG, TAT, TAC, GAT, GAC, CAT, or CAC,
    when the mutant base sequence has the mutation of (m), the bases at base Nos. 100 to 102 are ATT, ATC, or ATA,
    when the mutant base sequence has the mutation of (n), the bases at base Nos. 106 to 108 are GTT, GTC, GTA, or GTG,
    when the mutant base sequence has the mutation of (o), the bases at base Nos. 250 to 252 are TAA, TAG, or TGA, and
    when the mutant base sequence has the mutation of (p), the bases at base Nos. 391 to 393 are CGT, CGC, CGA, CGG, AGA, or AGG.

Item 3. A *Hydrogenophilus* bacterium, which produces the mutant acetolactate synthase III small subunit of Item 1.

Item 4. A *Hydrogenophilus* bacterium, including the mutant acetolactate synthase III small subunit gene of Item 2.

Item 5. A method of producing valine, including a step of culturing the *Hydrogenophilus* bacterium of Item 3 or 4 through use of carbon dioxide as a substantially sole carbon source.

Item 6. A counterselection marker for a *Hydrogenophilus* bacterium, including a streptomycin sensitivity gene of the following (7), (8), or (9):
(7) a streptomycin sensitivity gene formed of a base sequence set forth in SEQ ID NO: 3;
(8) a gene formed of a base sequence having 90% or more identity to the base sequence set forth in SEQ ID NO: 3, the gene encoding a polypeptide having activity of imparting streptomycin sensitivity to a streptomycin-resistant strain of a *Hydrogenophilus* bacterium; or
(9) a gene that hybridizes with DNA formed of a base sequence complementary to the base sequence set forth in SEQ ID NO: 3 under stringent conditions, and that encodes a polypeptide having activity of imparting streptomycin sensitivity to a streptomycin-resistant strain of a *Hydrogenophilus* bacterium.

Item 7. A method of producing a recombinant of a *Hydrogenophilus* bacterium, including using the counterselection marker of Item 6 and a streptomycin-resistant strain of a *Hydrogenophilus* bacterium.

Item 8. A method of producing a recombinant of a *Hydrogenophilus* bacterium, including the steps of:
(A) generating a labeling DNA fragment having a marker cassette, in which a DNA fragment containing a streptomycin sensitivity gene and a DNA fragment containing a gene for a positive selection marker are linked to each other, inserted between a 5' end-side region and a 3' end-side region of a DNA fragment formed of a mutant target gene of a *Hydrogenophilus* bacterium;
(B) performing an operation of introducing the labeling DNA fragment into a streptomycin-resistant strain of the *Hydrogenophilus* bacterium, followed by selecting recombinants in each of which a target gene of the streptomycin-resistant strain has been substituted with the labeling DNA fragment through use of the presence of a property of the positive selection marker as an indicator; and
(C) performing an operation of introducing the DNA fragment formed of the mutant target gene of the *Hydrogenophilus* bacterium into each of the recombinants, followed by selecting a recombinant in which a region of the labeling DNA on a genome has been substituted with the mutant target gene through use of streptomycin resistance as an indicator.

Item 9. The method according to Item 8, wherein the streptomycin sensitivity gene is a gene of the following (7), (8), or (9):

(7) a streptomycin sensitivity gene formed of a base sequence set forth in SEQ ID NO: 3;

(8) a gene formed of a base sequence having 90% or more identity to the base sequence set forth in SEQ ID NO: 3, the gene encoding a polypeptide having activity of imparting streptomycin sensitivity to the streptomycin-resistant strain of the *Hydrogenophilus* bacterium; or (9) a gene that hybridizes with DNA formed of a base sequence complementary to the base sequence set forth in SEQ ID NO: 3 under stringent conditions, and that encodes a polypeptide having activity of imparting streptomycin sensitivity to the streptomycin-resistant strain of the *Hydrogenophilus* bacterium.

Item 10. A method of producing a recombinant of a *Hydrogenophilus* bacterium, including the steps of:

(D) generating a labeling circular DNA containing a DNA fragment of a mutant target gene of a *Hydrogenophilus* bacterium, and a marker cassette in which a DNA fragment containing a streptomycin sensitivity gene and a DNA fragment containing a gene for a positive selection marker are linked to each other;

(E) performing an operation of introducing the labeling circular DNA into a streptomycin-resistant strain of the *Hydrogenophilus* bacterium, followed by selecting recombinants each having the labeling circular DNA linearized and inserted into a target gene of the streptomycin-resistant strain through use of the presence of a property of the positive selection marker as an indicator;

(F) selecting, from the recombinants, recombinants from each of which a region of the labeling DNA inserted on a genome has been eliminated, through use of streptomycin resistance as an indicator; and (G) selecting, from the recombinants selected in the step (F), a recombinant having a mutation introduced into the target gene.

Item 11. The method according to Item 10, wherein the streptomycin sensitivity gene is a gene of the following (7), (8), or (9):

(7) a streptomycin sensitivity gene formed of a base sequence set forth in SEQ ID NO: 3;

(8) a gene formed of a base sequence having 90% or more identity to the base sequence set forth in SEQ ID NO: 3, the gene encoding a polypeptide having activity of imparting streptomycin sensitivity to the streptomycin-resistant strain of the *Hydrogenophilus* bacterium; or (9) a gene that hybridizes with DNA formed of a base sequence complementary to the base sequence set forth in SEQ ID NO: 3 under stringent conditions, and that encodes a polypeptide having activity of imparting streptomycin sensitivity to the streptomycin-resistant strain of the *Hydrogenophilus* bacterium.

Item 12. A positive selection marker for a *Hydrogenophilus* bacterium, including a hygromycin resistance gene of the following (10), (11), or (12):

(10) a hygromycin resistance gene formed of a base sequence set forth in SEQ ID NO: 4;

(11) a gene formed of a base sequence having 90% or more identity to the base sequence set forth in SEQ ID NO: 4, the gene encoding a polypeptide having activity of imparting hygromycin resistance to a *Hydrogenophilus* bacterium; or

(12) a gene that hybridizes with DNA formed of a base sequence complementary to the base sequence set forth in SEQ ID NO: 4 under stringent conditions, and that encodes a polypeptide having activity of imparting hygromycin resistance to a *Hydrogenophilus* bacterium.

Item 13. A positive selection marker for a *Hydrogenophilus* bacterium, including a kanamycin resistance gene of the following (13), (14), or (15):

(13) a kanamycin resistance gene formed of a base sequence set forth in SEQ ID NO: 5 or 6;

(14) a gene formed of a base sequence having 90% or more identity to the base sequence set forth in SEQ ID NO: 5 or 6, the gene encoding a polypeptide having activity of imparting kanamycin resistance to a *Hydrogenophilus* bacterium; or

(15) a gene that hybridizes with DNA formed of a base sequence complementary to the base sequence set forth in SEQ ID NO: 5 or 6 under stringent conditions, and that encodes a polypeptide having activity of imparting kanamycin resistance to a *Hydrogenophilus* bacterium.

Advantageous Effects of the Invention

Measures to counter the increase in atmospheric carbon dioxide entail reduction of carbon dioxide emissions and fixation of emitted carbon dioxide. In order to reduce carbon dioxide emissions, solar, wind, geothermal, and similar energies are utilized in place of fossil energy. However, the utilization of such energies is not yet extensive enough to repress the buildup of atmospheric carbon dioxide. Consequently, there is need to enhance atmospheric carbon fixation or recycling of emitted carbon dioxide.

Carbon fixation of carbon dioxide can occur physically or chemically, but fixation utilizing living cells, avails organic substances that can consequently be utilized as food, feed, and fuel. In so doing, carbon dioxide itself becomes a resource that can be directly converted into valuable chemical products. Accordingly, the twin problems of global warming due to increased atmospheric carbon dioxide and scarcity of food, feed, and fuel can be solved.

Hydrogen-oxidizing bacteria can grow by utilizing the chemical energy generated by the reaction of hydrogen with oxygen and by using carbon dioxide as a sole carbon source. Since hydrogen-oxidizing bacteria can produce chemical products from a mixture of oxygen, hydrogen, and carbon dioxide gases as raw material, the cells can efficiently assimilate carbon from carbon dioxide and be cultured in a simple culture medium. Growth of typical hydrogen-oxidizing bacteria is generally slow, but that of *Hydrogenophilus* bacteria is exceptionally high. The Journal of Mitsubishi Research Institute No.34 1999 describes *Hydrogenophilus* bacteria as follows: "Their proliferative capacity is so high that their carbon fixation ability of carbon dioxide cannot be compared with that of plants, which truly indicates the high carbon dioxide fixation ability of microorganisms".

The *Hydrogenophilus* bacterium produces valine in an amount required for survival, but does not produce valine in an industrially applicable amount. The recombinant of the present invention has a mutation introduced into a valine production-associated gene on the genome of the *Hydrogenophilus* bacterium, and consequently, can efficiently produce valine.

As described above, the *Hydrogenophilus* bacterium has a particularly excellent carbon fixation ability of carbon dioxide among organisms having the carbon fixation ability of carbon dioxide. Accordingly, the use of the recombinant of the present invention enables production of valine through fixation of carbon from carbon dioxide on an industrial scale.

According to the present invention, the hygromycin resistance gene and the kanamycin resistance gene each of which can be used as a positive selection marker in the *Hydrogenophilus* bacterium have been provided. The streptomycin sensitivity gene that can be used as a counterselection marker by being used together with the streptomycin-resistant strain of the *Hydrogenophilus* bacterium has also been provided. Thus, the way has been paved for recombination and genome modification of the *Hydrogenophilus* bacterium. In particular, the finding of the streptomycin sensitivity gene that can be used as a counterselection marker has enabled recombination of the *Hydrogenophilus* bacterium to be repeatedly performed, to thereby allow its genome to be modified on a large scale. The marker does not remain in the genome, and hence, in comparing a recombinant strain of the *Hydrogenophilus* bacterium to its wild type strain, it has become possible to make a discussion by directly associating a difference between their phenotypes, that is, their properties with a difference between their genotypes.

DESCRIPTION OF EMBODIMENTS

Figure 1:
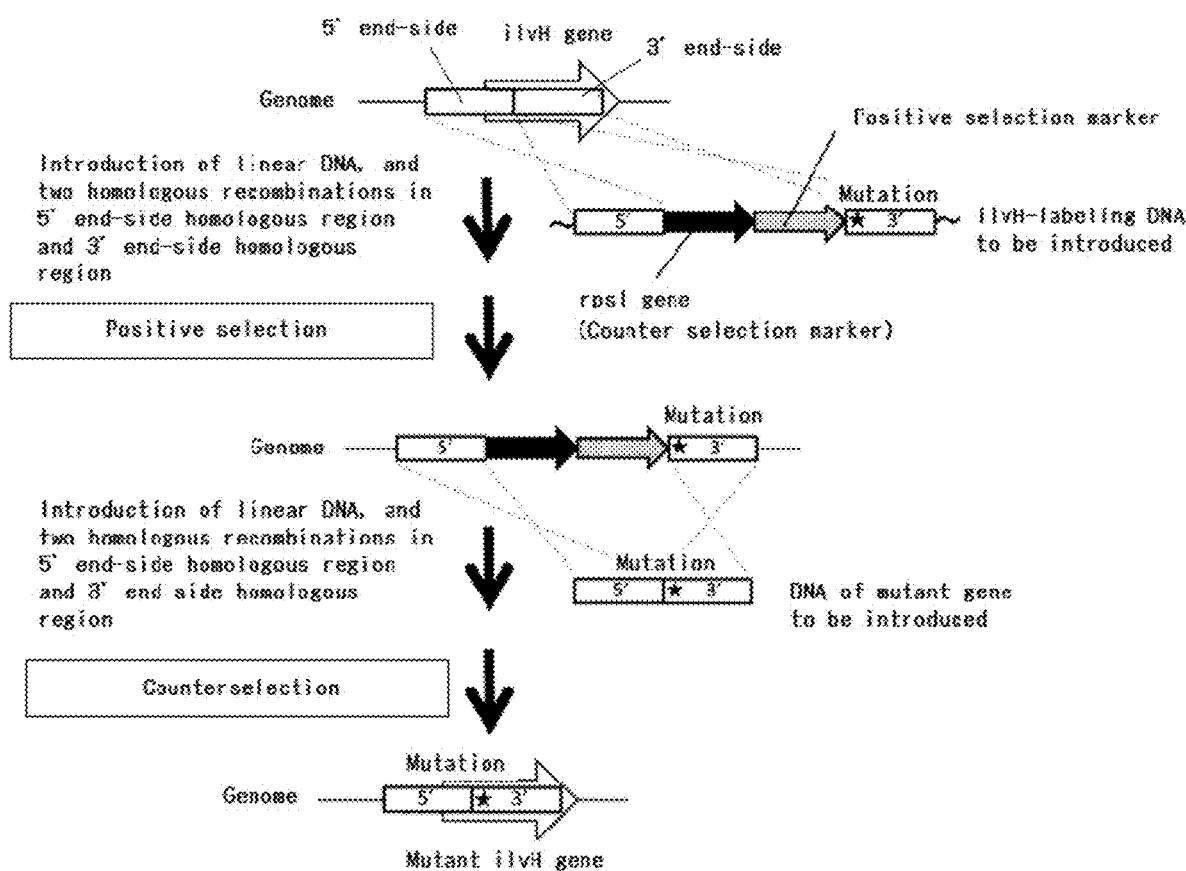
FIG. 1 is a diagram illustrating an example of a method of producing a recombinant of a *Hydrogenophilus* bacterium through use of a streptomycin sensitivity gene as a counterselection marker.

The present invention is described in detail below.

(1) *Hydrogenophilus* Bacterium Recombinant A *Hydrogenophilus* bacterium recombinant of the present invention produces a mutant acetolactate synthase III small subunit of any one of the following (1) to (3).

(1) A mutant acetolactate synthase III small subunit formed of a mutant amino acid sequence having a mutation of any one of the following (a) to (h) in an amino acid sequence set forth in SEQ ID NO: 1:

(a) a substitution of Asn at amino acid No. 11 with Asp, His, or Ala;

(b) a substitution of Gly at amino acid No. 14 with Asp or Ala;

(c) a substitution of Ser at amino acid No. 17 with Phe;

(d) a substitution of Asn at amino acid No. 29 with Lys, Tyr, Asp, or His;

(e) a substitution of Thr at amino acid No. 34 with Ile;

(f) a substitution of Ala at amino acid No. 36 with Val;

(g) a deletion of Arg at amino acid No. 84 and all subsequent amino acids; and (h) a substitution of Leu at amino acid No. 131 with Arg.

SEQ ID NO: 1 sets forth the amino acid sequence of the naturally occurring acetolactate synthase III small subunit of *Hydrogenophilus thermoluteolus*.

(2) A mutant acetolactate synthase III small subunit that is formed of an amino acid sequence having 90% or more, preferably 95% or more, even more preferably 98% or more, still more preferably 99% or more identity to the mutant amino acid sequence described in (1), and that has acetolactate synthase III small subunit activity and is suppressed in feedback inhibition by valine, provided that when the mutant amino acid sequence has the mutation of (a), the amino acid at amino acid No. 11 is Asp, His, or Ala, when the mutant amino acid sequence has the mutation of (b), the amino acid at amino acid No. 14 is Asp or Ala, when the mutant amino acid sequence has the mutation of (c), the amino acid at amino acid No. 17 is Phe, when the mutant amino acid sequence has the mutation of (d), the amino acid at amino acid No. 29 is Lys, Tyr, Asp, or His, when the mutant amino acid sequence has the mutation of (e), the amino acid at amino acid No. 34 is Ile, when the mutant amino acid sequence has the mutation of (f), the amino acid at amino acid No. 36 is Val, when the mutant amino acid sequence has the mutation of (g), the amino acid at amino acid No. 84 and all subsequent amino acids are deleted, and when the mutant amino acid sequence has the mutation of (h), the amino acid at amino acid No. 131 is Arg.

In the present invention, the identity of the amino acid sequence is a value calculated with GENETYX ver. 17 (manufactured by Genetyx Corporation).

(3) A mutant acetolactate synthase III small subunit that is formed of an amino acid sequence having one or a plurality of amino acids deleted, substituted, or added in the mutant amino acid sequence described in (1), and that has acetolactate synthase III small subunit activity and is suppressed in feedback inhibition by valine, provided that when the mutant amino acid sequence has the mutation of (a), the amino acid at amino acid No. 11 is Asp, His, or Ala, when the mutant amino acid sequence has the mutation of (b), the amino acid at amino acid No. 14 is Asp or Ala, when the mutant amino acid sequence has the mutation of (c), the amino acid at amino acid No. 17 is Phe, when the mutant amino acid sequence has the mutation of (d), the amino acid at amino acid No. 29 is Lys, Tyr, Asp, or His, when the mutant amino acid sequence has the mutation of (e), the amino acid at amino acid No. 34 is Ile, when the mutant amino acid sequence has the mutation of (f), the amino acid at amino acid No. 36 is Val, when the mutant amino acid sequence has the mutation of (g), the amino acid at amino acid No. 84 and all subsequent amino acids are deleted, and when the mutant amino acid sequence has the mutation of (h), the amino acid at amino acid No. 131 is Arg.

In the present invention, the plurality is, for example, from 1 to 5, especially from 1 to 3, especially 1 or 2, in particular, 1.

An acetolactate synthase produces acetolactate from pyruvic acid. In the present invention, the fact that a polypeptide to be tested has acetolactate synthase III small subunit activity is verified by the fact that acetolactate synthase activity is detected under coexistence with an acetolactate synthase III large subunit. The acetolactate synthase activity is measured by: mixing 100 mM potassium phosphate (pH 7.5), 50 mM sodium pyruvate, 10 mM $MgCl_2$, 0.1 mM thiamine pyrophosphate, 0.1 mM flavin adenine dinucleotide, and the polypeptide to be tested; and using a reduction in absorbance at 333 nm ($\varepsilon$=17.5/M·cm) showing absorption by pyruvic acid as an indicator.

In the present invention, the fact that the polypeptide to be tested is suppressed in feedback inhibition by valine is verified by detecting acetolactate synthase activity in the presence of valine. When the polypeptide to be tested is enhanced, even if only slightly, in acetolactate synthase activity under coexistence with the acetolactate synthase III large subunit in the presence of a certain concentration of valine as compared to wild-type (naturally occurring) acetolactate synthase III, it is judged that the feedback inhibition by valine is suppressed.

An example of the *Hydrogenophilus* bacterium recombinant of the present invention is a *Hydrogenophilus* bacterium recombinant having a mutant acetolactate synthase III small subunit gene of any one of the following (4) to (6) on the genome thereof.

A particular example thereof is a *Hydrogenophilus* bacterium recombinant in which the naturally occurring acetolactate synthase III small subunit gene on the genome has been substituted with the mutant acetolactate synthase III small subunit gene of any one of the following (4) to (6).

(4) A gene formed of a mutant base sequence having a mutation of any one of the following (i) to (p) in a base sequence set forth in SEQ ID NO: 2:
  (i) a substitution of AAC at base Nos. 31 to 33 with GAT, GAC, CAT, CAC, GCT, GCC, GCA, or GCG;
  (j) a substitution of GGC at base Nos. 40 to 42 with GAT, GAC, GCT, GCC, GCA, or GCG;
  (k) a substitution of TCG at base Nos. 49 to 51 with TTT or TTC;
  (l) a substitution of AAC at base Nos. 85 to 87 with AAA, AAG, TAT, TAC, GAT, GAC, CAT, or CAC;
  (m) a substitution of ACC at base Nos. 100 to 102 with ATT, ATC, or ATA;
  (n) a substitution of GCA at base Nos. 106 to 108 with GTT, GTC, GTA, or GTG;
  (o) a substitution of CGC at base Nos. 250 to 252 with TAA, TAG, or TGA; and
  (p) a substitution of CTC at base Nos. 391 to 393 with CGT, CGC, CGA, CGG, AGA, or AGG.

SEQ ID NO: 2 sets forth the base sequence of the naturally occurring acetolactate synthase III small subunit gene of *Hydrogenophilus thermoluteolus*.

(5) A gene formed of a base sequence having 90% or more, preferably 95% or more, more preferably 98% or more, still more preferably 99% or more identity to the mutant base sequence described in (4), the gene encoding a mutant acetolactate synthase III small subunit that has acetolactate synthase III small subunit activity and is suppressed in feedback inhibition by valine,
  provided that
    when the mutant base sequence has the mutation of (i), the bases at base Nos. 31 to 33 are GAT, GAC, CAT, CAC, GCT, GCC, GCA, or GCG,
    when the mutant base sequence has the mutation of (j), the bases at base Nos. 40 to 42 are GAT, GAC, GCT, GCC, GCA, or GCG,
    when the mutant base sequence has the mutation of (k), the bases at base Nos. 49 to 51 are TTT or TTC,
    when the mutant base sequence has the mutation of (l), the bases at base Nos. 85 to 87 are AAA, AAG, TAT, TAC, GAT, GAC, CAT, or CAC,
    when the mutant base sequence has the mutation of (m), the bases at base Nos. 100 to 102 are ATT, ATC, or ATA,
    when the mutant base sequence has the mutation of (n), the bases at base Nos. 106 to 108 are GTT, GTC, GTA, or GTG,
    when the mutant base sequence has the mutation of (o), the bases at base Nos. 250 to 252 are TAA, TAG, or TGA, and
    when the mutant base sequence has the mutation of (p), the bases at base Nos. 391 to 393 are CGT, CGC, CGA, CGG, AGA, or AGG.

In the present invention, the identity of the base sequence is a value calculated with GENETYX ver. 17 (manufactured by Genetyx Corporation).

(6) A gene that hybridizes with DNA formed of a base sequence complementary to the mutant base sequence described in (4) under stringent conditions, and that encodes a mutant acetolactate synthase III small subunit having acetolactate synthase III small subunit activity and being suppressed in feedback inhibition by valine,
  provided that
    when the mutant base sequence has the mutation of (i), the bases at base Nos. 31 to 33 are GAT, GAC, CAT, CAC, GCT, GCC, GCA, or GCG,
    when the mutant base sequence has the mutation of (j), the bases at base Nos. 40 to 42 are GAT, GAC, GCT, GCC, GCA, or GCG,
    when the mutant base sequence has the mutation of (k), the bases at base Nos. 49 to 51 are TTT or TTC,
    when the mutant base sequence has the mutation of (l), the bases at base Nos. 85 to 87 are AAA, AAG, TAT, TAC, GAT, GAC, CAT, or CAC,
    when the mutant base sequence has the mutation of (m), the bases at base Nos. 100 to 102 are ATT, ATC, or ATA,
    when the mutant base sequence has the mutation of (n), the bases at base Nos. 106 to 108 are GTT, GTC, GTA, or GTG,
    when the mutant base sequence has the mutation of (o), the bases at base Nos. 250 to 252 are TAA, TAG, or TGA, and
    when the mutant base sequence has the mutation of (p), the bases at base Nos. 391 to 393 are CGT, CGC, CGA, CGG, AGA, or AGG.

In the present invention, "stringent conditions" means hybridization with 6×SSC solution at temperatures from 50 to 60° C. for 16 hours, followed by washing with 0.1×SSC solution.

Examples of *Hydrogenophilus* bacteria include *Hydrogenophilus thermoluteolus*, *Hydrogenophilus halorhabdus*, *Hydrogenophilus denitrificans*, *Hydrogenophilus hirschii*, *Hydrogenophilus islandicus*, and strain Mar3 of the genus *Hydrogenophilus* (*Hydrogenophilus* sp. Mar3). In particular, *Hydrogenophilus thermoluteolus* is preferable because its superior growth rate enables top-level carbon fixation from carbon dioxide among carbon dioxide fixing microorganisms.

*Hydrogenophilus* bacteria have been easily isolated from diverse regions everywhere on the earth. A preferable strain of *Hydrogenophilus thermoluteolus* is strain TH-1 (NBRC 14978). *Hydrogenophilus thermoluteolus* strain TH-1 (NBRC 14978) exhibits comparatively rapid growth rate among carbon dioxide fixing microorganisms (Agricultural and Biological Chemistry, 41, 685-690 (1977)). *Hydrogenophilus thermoluteolus* strain NBRC 14978 is internationally deposited under the Budapest Treaty, and is thus available to the general public.

(2) Method for Producing Valine

To produce valine using the *Hydrogenophilus* bacterium recombinant described above, the recombinant can be cultured using an inorganic defined or organic complex culture medium while supplying a mixed gas containing hydrogen, oxygen, and carbon dioxide.

The supplied gas is preferably a mixture of hydrogen, oxygen, and carbon dioxide. However, different kinds of gases can be mixed within to the extent that lactic acid can be efficiently produced.

*Hydrogenophilus* bacteria can grow using hydrogen as a source of energy and using carbon dioxide as a sole carbon source, and thus, efficiently assimilate the carbon in carbon dioxide to produce the above-described compounds by using substantially only carbon dioxide (in particular, by using only carbon dioxide) as a carbon source. Therefore, using an inorganic culture medium that does not contain carbon sources such as organic substances and carbonates, namely, carrying out culture using substantially only carbon dioxide (in particular, using only carbon dioxide) as a carbon source is preferable. Using substantially only carbon dioxide as a carbon source encompasses cases in which an unavoidable amount of other carbon sources is mixed within. Furthermore, a culture medium containing organic substances such as sugar, organic acids, and amino acids, as well as carbonates, can also be used without supplying carbon dioxide.

The pH of the culture medium is preferably 6.2 to 8, more preferably 6.4 to 7.4, and even more preferably 6.6 to 7. When the pH is within this range, the bacteria grow well and mixed gases dissolve better into the culture medium, and valine can be produced more efficiently.

When batch culture is utilized, mixed gases can be entrapped within an airtight culture container and static culture or shaking culture can be carried out. When continuous culture is utilized, mixed gas can be continuously supplied into an airtight culture container and shaking culture can be carried out, or the transformant can be cultured using an airtight culture container while introducing mixed gases into the culture medium by bubbling. Shaking culture is preferable in that better dissolution of mixed gases into the culture medium can be achieved.

The volume ratio of hydrogen, oxygen, and carbon dioxide (hydrogen:oxygen:carbon dioxide) in the supplied gas mixture is preferably 1.75 to 7.5:1:0.25 to 3, more preferably 5 to 7.5:1:1 to 2, and even more preferably 6.25 to 7.5:1:1.5. When the volume ratio is within this range, bacteria grow well, and the target compound can be produced efficiently.

The supply rate of mixed gases or raw material gases can be 10.5 to 60 L/hour, in particular 10.5 to 40 L/hour, in particular 10.5 to 21 L/hour, per 1 L of culture medium. When the supply rate is within this range, transformants grow well and valine can be produced efficiently, and the volume of unutilized mixed gases can be minimized.

The culture temperature is preferably 35 to 55° C., more preferably 37 to 52° C., and furthermore preferably 50 to 52° C. When the temperature is within this range, transformants grow well, and valine can be produced efficiently.

The target compound valine is produced in the reaction solution by culturing in the above-described manner. Collecting the reaction solution allows for recovery of the valine. However, valine can furthermore be separated from the reaction solution by employing publicly known methods. Such publicly known methods include ion-exchange resin, concentration, crystallization and adsorption and elution using activated carbon.

(3) Method of Generating Recombinant of *Hydrogenophilus* Bacterium

A gene on a chromosome can be substituted with a mutant gene by generating the mutant gene through PCR or the like, transforming a bacterium with DNA containing the mutant gene, and causing homologous recombination between the mutant gene and the gene on the genome. That is, a mutation can be introduced into a gene on a chromosome. An enzyme protein encoded by the mutant gene has a three-dimensional structure different from that of a wild-type enzyme protein, resulting in a change in function.

The modification of a gene on a genome utilizing homologous recombination as described above is unprecedented in *Hydrogenophilus* bacteria. In the present invention, a counterselection method involving utilizing a streptomycin-resistant strain and a streptomycin sensitivity gene in a *Hydrogenophilus* bacterium has been developed, and genetic modification has been performed on the basis of the principle of site-directed incorporation of a marker by homologous recombination and elimination of the marker by a second homologous recombination.

In this method, a streptomycin sensitivity gene of the following (7), (8), or (9) is used as a counterselection marker. Those streptomycin sensitivity genes function in the *Hydrogenophilus* bacterium.

(7) A streptomycin sensitivity gene formed of a base sequence set forth in SEQ ID NO: 3

(8) A gene formed of a base sequence having 90% or more, preferably 95% or more, even more preferably 98% or more, still more preferably 99% or more identity to the base sequence set forth in SEQ ID NO: 3, the gene encoding a polypeptide having activity of imparting streptomycin sensitivity to a streptomycin-resistant strain of a *Hydrogenophilus* bacterium (9) A gene that hybridizes with DNA formed of a base sequence complementary to the base sequence set forth in SEQ ID NO: 3 under stringent conditions, and that encodes a polypeptide having activity of imparting streptomycin sensitivity to a streptomycin-resistant strain of a *Hydrogenophilus* bacterium Examples of the streptomycin sensitivity genes of (8) and (9) include genes of the following (r), (s), and (t):

(r) a streptomycin sensitivity gene formed of a base sequence in which, in SEQ ID NO: 3, AAA at base Nos. 127 to 129 are substituted with CGT, CGC, CGA, CGG, AGA, AGG, AAT, AAC, ACT, ACC, ACA, ACG, ATT, ATC, or ATA;

(s) a streptomycin sensitivity gene formed of a base sequence in which, in SEQ ID NO: 3, AAA at base Nos. 262 to 264 are substituted with CGT, CGC, CGA, CGG, AGA, AGG, GAA, or GAG; and (t) a streptomycin sensitivity gene formed of a base sequence in which, in SEQ ID NO: 3, CCG at base Nos. 271 to 273 are substituted with TTA, TTG, CTT, CTC, CTA, CTG, CAA, or CAG.

As a preferred promoter for causing a marker gene to be expressed in the *Hydrogenophilus* bacterium, there are given, for example, a tac promoter, a lac promoter, a trc promoter, and promoters OXB1 and OXB11 to OXB20 from Oxford Genetics Ltd. As a preferred terminator, there are given, for example, the T1T2 terminator of the rRNA operon rrnB of *Escherichia coli*, and the t0 transcriptional terminator of bacteriophage λ.

The fact that a gene to be tested is a gene encoding a polypeptide having activity of imparting streptomycin sensitivity to a streptomycin-resistant strain of a *Hydrogenophilus* bacterium is verified by the fact that a streptomycin-resistant strain having the gene to be tested introduced thereinto is inhibited from growth in the presence of streptomycin (50 μg/mL or more) to the same degree as a wild-type *Hydrogenophilus* bacterium.

An example of the method of producing a recombinant of a *Hydrogenophilus* bacterium through use of the counterselection marker described above is a method including the following steps (A) to (C) (first method, FIG. 1):

(A) generating a labeling DNA fragment having a marker cassette, in which a DNA fragment containing a streptomycin sensitivity gene and a DNA fragment containing a gene for a positive selection marker are linked to each other, inserted between a 5' end-side region and a 3' end-side region of a DNA fragment formed of a mutant target gene of a *Hydrogenophilus* bacterium;

(B) performing an operation of introducing the labeling DNA fragment into a streptomycin-resistant strain of the *Hydrogenophilus* bacterium, followed by selecting recombinants in each of which a target gene of the streptomycin-resistant strain has been substituted with the labeling DNA fragment through use of the presence of a property of the positive selection marker as an indicator; and (C) performing an operation of introducing the DNA fragment formed of the mutant target gene of the *Hydrogenophilus* bacterium into each of the recombinants, followed by selecting a recombinant in which a region of the labeling DNA on a genome has been substituted with the mutant target gene through use of streptomycin resistance as an indicator.

(A) Generation of Labeling DNA Fragment

A site-directed mutagenesis method for introducing a mutation of interest (e.g., substitution, deletion, or addition (including insertion)) into a target gene is well known. For example, a target gene of the *Hydrogenophilus* bacterium which has the mutation introduced thereinto may be obtained by performing PCR through use of a primer set in which one primer has the mutation of interest incorporated thereinto, and through use of the genomic DNA of the *Hydrogenophilus* bacterium as a template.

In this case, it is appropriate that: the target gene be divided into two parts, i.e., a 5' end-side region and a 3' end-side region; the regions be each amplified by PCR; and one or a plurality of mutations be introduced into any one, or both, of the regions.

It is appropriate that the amplified 5' end-side region and 3' end-side region be linked to a vector that can be used in a host, such as *Escherichia coli*.

Next, the marker cassette to be inserted between the 5' end-side region and the 3' end-side region on the vector is produced. The marker cassette is such that a streptomycin sensitivity gene that functions in the *Hydrogenophilus* bacterium and a positive selection marker gene that functions in the *Hydrogenophilus* bacterium are linked to each other adjacently or with DNA of about 10,000 base pairs or less being interposed therebetween.

Next, it is appropriate that the marker cassette be inserted between the 5' end-side region and the 3' end-side region of the mutant target gene on the vector having inserted thereinto the DNA fragment formed of the mutant target gene of the *Hydrogenophilus* bacterium. Further, it is appropriate that, in accordance with a conventional method, the host be transformed with the resultant vector, and the vector be extracted from the transformant.

Next, it is appropriate that the vector be linearized through cleavage between the 5' end-side region and the 3' end-side region of the mutant target gene with a restriction enzyme, to thereby provide a labeling DNA fragment. The cleavage is performed so that the marker cassette is brought into a state of being interposed between the 5' end-side region and the 3' end-side region of the mutant target gene.

The gene of the above-mentioned (7), (8), or (9) may be used as the streptomycin sensitivity gene that functions in the *Hydrogenophilus* bacterium.

No positive selection marker gene that functions in the *Hydrogenophilus* bacterium has hitherto been known at all.

In the present invention, it has been found that a hygromycin resistance gene of the following (10), (11), or (12) functions in the *Hydrogenophilus* bacterium, and can be used as a positive selection marker.

(10) A hygromycin resistance gene formed of a base sequence set forth in SEQ ID NO: 4

(11) A gene formed of a base sequence having 90% or more, preferably 95% or more, more preferably 98% or more, still more preferably 99% or more identity to the base sequence set forth in SEQ ID NO: 4, the gene encoding a polypeptide having activity of imparting hygromycin resistance to a *Hydrogenophilus* bacterium

(12) A gene that hybridizes with DNA formed of a base sequence complementary to the base sequence set forth in SEQ ID NO: 4 under stringent conditions, and that encodes a polypeptide having activity of imparting hygromycin resistance to a *Hydrogenophilus* bacterium The fact that a gene to be tested is a gene encoding a polypeptide having activity of imparting hygromycin resistance to the *Hydrogenophilus* bacterium is verified by the fact that the *Hydrogenophilus* bacterium having the gene to be tested introduced thereinto is enhanced in growth in the presence of hygromycin (100 µg/mL) as compared to the wild-type *Hydrogenophilus* bacterium before the introduction of the gene to be tested (e.g., the fact of being capable of growing in the presence of hygromycin (100 µg/mL) unlike the wild-type *Hydrogenophilus* bacterium before the introduction of the gene to be tested).

In the present invention, it has also been found that a kanamycin resistance gene of the following (13), (14), or (15) functions in the *Hydrogenophilus* bacterium, and can be used as a positive selection marker.

(13) A kanamycin resistance gene formed of a base sequence set forth in SEQ ID NO: 5 or 6

(14) A gene formed of a base sequence having 90% or more, preferably 95% or more, more preferably 98% or more, still more preferably 99% or more identity to the base sequence set forth in SEQ ID NO: 5 or 6, the gene encoding a polypeptide having activity of imparting kanamycin resistance to a *Hydrogenophilus* bacterium

(15) A gene that hybridizes with DNA formed of a base sequence complementary to the base sequence set forth in SEQ ID NO: 5 or 6 under stringent conditions, and that encodes a polypeptide having activity of imparting kanamycin resistance to a *Hydrogenophilus* bacterium The fact that a gene to be tested is a gene encoding a polypeptide having activity of imparting kanamycin resistance to the *Hydrogenophilus* bacterium is verified by the fact that the *Hydrogenophilus* bacterium having the gene to be tested introduced thereinto is enhanced in growth in the presence of kanamycin (50 µg/mL) as compared to the wild-type *Hydrogenophilus* bacterium before the introduction of the gene to be tested (e.g., the fact of being capable of growing in the presence of kanamycin (50 µg/mL) unlike the wild-type *Hydrogenophilus* bacterium before the introduction of the gene to be tested).

(B) Positive Selection

In selecting recombinants in each of which the target gene on the genome of the *Hydrogenophilus* bacterium has been substituted with the labeling DNA fragment through homologous recombination with the labeling DNA fragment, it is appropriate to select recombinants each of which has gained a property of the positive selection marker, for example, recombinants each of which has become hygromycin-resistant or kanamycin-resistant.

In order to perform counterselection through use of the streptomycin sensitivity gene as a counterselection marker in the next step, a streptomycin-resistant strain of the *Hydrogenophilus* bacterium is used as a host. When a bacterial suspension of the *Hydrogenophilus* bacterium is applied to a solid medium containing about 50 μg/mL to about 500 μg/mL of streptomycin, and is cultured, a streptomycin-resistant strain generally emerges at a certain ratio.

An operation of introducing the labeling DNA fragment into the streptomycin-resistant strain is performed, and recombinants in each of which the target gene on the genome of the streptomycin-resistant strain has been substituted with the labeling DNA fragment are selected through use of the property of the positive selection marker as an indicator. The labeling DNA fragment to be introduced may further have extra nucleotides added to both ends thereof (5' end of the 5' end-side region of the mutant target gene, and 3' end of the 3' end-side region of the mutant target gene). The recombinants to be obtained are streptomycin-sensitive.

The introduction of DNA into cells of the *Hydrogenophilus* bacterium may be performed by a known method, such as a calcium chloride method, a calcium phosphate method, a DEAE-dextran mediated transfection method, or an electric pulse method.

(C) Counterselection

Next, in order to delete the marker cassette inserted into the mutant target gene, homologous recombination using the DNA fragment formed of the mutant target gene is performed.

The vector having the mutant target gene of the *Hydrogenophilus* bacterium inserted thereinto is linearized by being cleaved in such a manner that the mutant target gene is not divided. It is appropriate that an operation of introducing the linear DNA fragment into the streptomycin-sensitive strains (recombinants in each of which the target gene has been substituted with the labeling DNA fragment) be performed, and a strain that has become streptomycin-resistant be selected. It is also preferred that a strain that is streptomycin-resistant and has lost the property of the positive selection marker be selected. Thus, a recombinant from which the marker cassette inserted into the mutant target gene has been eliminated, that is, a recombinant having the mutation of interest introduced into the target gene is obtained.

Figure 2:
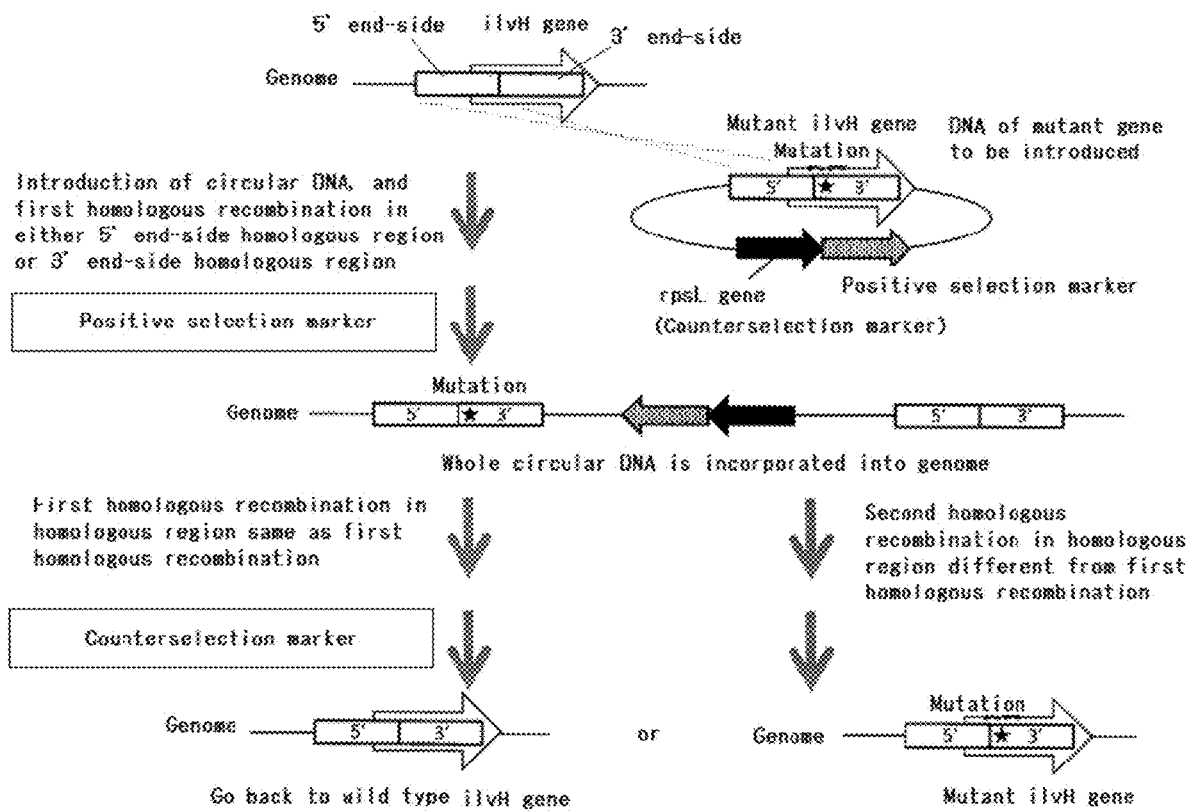
FIG. 2 is a diagram illustrating another example of the method of producing a recombinant of a *Hydrogenophilus* bacterium through use of a streptomycin sensitivity gene as a counterselection marker.

Another example of the method of producing a recombinant of a *Hydrogenophilus* bacterium through use of the counterselection marker described above is a method including the following steps (D) to (G) (second method, FIG. 2):

(D) generating labeling circular DNA containing a DNA fragment of a mutant target gene of a *Hydrogenophilus* bacterium, and a marker cassette in which a DNA fragment containing a streptomycin sensitivity gene and a DNA fragment containing a gene for a positive selection marker are linked to each other;

(E) performing an operation of introducing the labeling circular DNA into a streptomycin-resistant strain of the *Hydrogenophilus* bacterium, followed by selecting recombinants each having the labeling circular DNA linearized and inserted into a target gene of the streptomycin-resistant strain through use of the presence of a property of the positive selection marker as an indicator;

(F) selecting, from the recombinants, recombinants from each of which a region of the labeling DNA inserted on a genome has been eliminated, through use of streptomycin resistance as an indicator; and (G) selecting, from the recombinants selected in the step (F), a recombinant having a mutation introduced into the target gene.

(D) Generation of Labeling Circular DNA

Circular DNA containing a target gene of the *Hydrogenophilus* bacterium which has a mutation introduced thereinto, and the marker cassette is produced. The marker cassette is as described for the step (A) of the first method. It is appropriate that the size of the circular DNA be about 15,000 base pairs or less as a whole.

(E) Positive Selection

It is appropriate that an operation of introducing the resultant labeling circular DNA into a streptomycin-resistant strain of the *Hydrogenophilus* bacterium be performed, and recombinants each of which has gained a property of the positive selection marker, for example, recombinants each of which has become hygromycin-resistant or kanamycin-resistant be selected. Thus, recombinants each having the labeling circular DNA linearized and inserted into the target gene on the genome of the *Hydrogenophilus* bacterium as a result of homologous recombination with the 5' end-side region or the 3' end-side region of the target gene are selected. That is, on the genome of each of these recombinants, the DNA containing the marker cassette is inserted between the mutant target gene and the naturally occurring target gene. Accordingly, the recombinants to be obtained are streptomycin-sensitive.

(F) Counterselection

From the resultant recombinants, strains each of which has become streptomycin-resistant, preferably strains each of which is streptomycin-resistant and has lost the property of the positive selection marker are selected, and thus there are obtained recombinants from each of which the region between the mutant target gene and the naturally occurring target gene on the genome has been eliminated through the occurrence of a second homologous recombination between the two genes. The target gene on the genome of each of the recombinants to be obtained is the naturally occurring one in some cases, and is the mutant one in other cases. When the homologous recombination occurs in the same region as the region in which the first homologous recombination has occurred out of the 5' end-side region or the 3' end-side region of the target gene, the resultant target gene is the wild type; and when the homologous recombination occurs in the region different from the region in which the first homologous recombination has occurred out of the 5' end-side region or the 3' end-side region of the target gene, the resultant target gene has the mutation introduced thereinto.

(G) Selection of Recombinant Having Mutant Target Gene

From the recombinants obtained in the step (F), a strain having the mutation of interest introduced into the target gene is selected. It is appropriate that the base sequence of the target gene of the resultant recombinant be determined to verify the introduction of the mutation.

When the target gene is an acetolactate synthase III small subunit gene, and the mutant target gene of interest is a gene encoding a mutant acetolactate synthase III small subunit having acetolactate synthase III small subunit activity and being suppressed in feedback inhibition by valine, it is appropriate that a strain enhanced in growth in the presence of valine as compared to the wild strain of the *Hydrogenophilus* bacterium subjected to the mutation be selected.

The mutant acetolactate synthase III small subunit gene formed of a base sequence in which GGC at base Nos. 40 to 42 of SEQ ID NO: 2 are substituted with GAC contains a recognition sequence for a restriction enzyme MluI as a result of the mutation. Accordingly, it is appropriate that, for the recombinants obtained in the step (F), the target gene be amplified by colony PCR, and it be verified that the amplified DNA fragment is cleaved with the restriction enzyme MluI.

As described above, the combination of the positive selection marker and the counterselection marker each of which functions in the *Hydrogenophilus* bacterium has enabled the modification of a gene on the genome utilizing homologous recombination.

The *Hydrogenophilus* bacterium recombinant having an enhanced valine-producing ability of the present invention can also be generated by the method described above.

The number of positive selection markers that can be used in the *Hydrogenophilus* bacterium is limited, but a recombination operation can be repeatedly performed any number of times by combining the positive selection marker and the counterselection marker, and thus a plurality of genes on the genome can be modified.

*Hydrogenophilus* bacteria grow under autotrophic conditions. However, since they can grow under heterotrophic conditions as well, the culture medium which is used to culture a host or *Hydrogenophilus* bacterium recombinant can either be an inorganic culture medium or an organic culture medium. An organic culture medium comprising sugar, organic acids, amino acid, and the like can be used. The pH of the culture medium can be adjusted to approximately 6.2 to 8.

In any of the cases, culture can be carried out while supplying a mixture of gases containing hydrogen, oxygen, and carbon dioxide, and preferably a mixture of gases consisting of hydrogen, oxygen, and carbon dioxide. When using an organic culture medium, a mixture of gases containing hydrogen, oxygen, and carbon dioxide, for example air, can be used for aeration. When carbon dioxide gas is not supplied, a culture medium containing a carbonate as a carbon source can be used. Mixed gases can be entrapped within or continuously supplied into an airtight culture container, and can be dissolved into the culture medium by means of shaking culture. Alternatively, the culture container can be an airtight or open type, and mixed gases can be dissolved into the culture medium by bubbling.

The volume ratio of hydrogen, oxygen, and carbon dioxide within the supplied gas (hydrogen: oxygen: carbon dioxide) is preferably 1.75 to 7.5:1:0.25 to 3, more preferably 5 to 7.5:1:1 to 2, and furthermore preferably 6.25 to 7.5:1:1.5. *Hydrogenophilus* bacteria are thermophilic bacteria, and thus the culture temperature is preferably 35 to 55° C., more preferably 37 to 52° C., and even more preferably 50 to 52° C.

EXAMPLES (1) Acquisition of Streptomycin-Resistant Strain

A *Hydrogenophilus thermoluteolus* TH-1 strain (NBRC 14978) (hereinafter sometimes referred to as "TH-1 strain") was inoculated into a test tube having placed therein 5 mL of A-liquid medium [having 3.0 g of $(NH_4)_2SO_4$, 1.0 g of $KH_2PO_4$, 2.0 g of $K_2HPO_4$, 0.25 g of NaCl, 0.014 g of $FeSO_4 \cdot 7H_2O$, 0.5 g of $MgSO_4 \cdot 7H_2O$, 0.03 g of $CaCl_2$, 4.0 mg of $MoO_3$, 28 mg of $ZnSO_4 \cdot 7H_2O$, 2.0 mg of $CuSO_4 \cdot 5H_2O$, 4.0 mg of $H_3BO_3$, 4.0 mg of $MnSO_4 \cdot 5H_2O$, and 4.0 mg of $CoCl_2 \cdot 6H_2O$ dissolved in 1 L of distilled water (pH 7.0)] using a platinum loop, the test tube was filled with a mixed gas of $H_2:O_2:CO_2=7.5:1:1.5$, and shaking culture was performed at 50° C. The culture liquid after 24 hours was applied to A-solid medium containing 500 μg/mL of streptomycin [having 3.0 g of $(NH_4)_2SO_4$, 1.0 g of $KH_2PO_4$, 2.0 g of $K_2HPO_4$, 0.25 g of NaCl, 0.014 g of $FeSO_4 \cdot 7H_2O$, 0.5 g of $MgSO_4 \cdot 7H_2O$, 0.03 g of $CaCl_2$, 4.0 mg of $MoO_3$, 28 mg of $ZnSO_4 \cdot 7H_2O$, 2.0 mg of $CuSO_4 \cdot 5H_2O$, 4.0 mg of $H_3BO_3$, 4.0 mg of $MnSO_4 \cdot 5H_2O$, 4.0 mg of $CoCl_2 \cdot 6H_2O$, and 15 g of agar dissolved in 1 L of distilled water (pH 7.0)], and culture was performed in a chamber filled with a mixed gas of $H_2:O_2:CO_2=7.5:1:1.5$ at 50° C. for 60 hours.

As a result, the formation of three colonies was able to be recognized on the A-solid medium containing 500 μg/mL of streptomycin. Those grown strains were streptomycin-resistant strains of the TH-1 strain, and one of the strains was named NOC269 strain.

(2) Construction of Marker Cassette (2-1) Preparation of Counterselection Marker Genomic DNA was extracted from the wild strain (streptomycin-sensitive strain) of the TH-1 strain in accordance with a conventional method. Through use of the extracted genomic DNA as a template, a DNA fragment containing a rpsL gene, which was a streptomycin sensitivity gene, encoding ribosomal protein S12, was amplified by a PCR method. The following primers were used for the PCR. The PCR was performed by a conventional method using "DNA Thermal Cycler" manufactured by Life Technologies Corporation and using KOD FX Neo (manufactured by Toyobo Co., Ltd.) as a reaction reagent.

Primers for amplifying wild-type rpsL gene of TH-1 strain

```
                                                (SEQ ID NO: 7)
(a-1) 5'-ATACGCGTCCTCCGATGCGTCGTAAGGGAAACGTC-3'

(SEQ ID NO: 8)
(b-1) 5'-ATAGTCGACTTATTTCTTGCCCGCAGCGGCGCCCG-3'
```

The primer (a-1) has an MluI restriction enzyme site added thereto, and the primer (b-1) has a SalI restriction enzyme site added thereto.

(2-2) Preparation of Positive Selection Marker

Through use of DNA of a plasmid pJR225 (GenBank: K01193) [Gene, 25, 179-188 (1983)] containing a hygromycin resistance gene (hereinafter sometimes referred to as "hph") sequence as a template, a DNA fragment containing the hph gene was amplified by a PCR method. The following primers were used for the PCR. The PCR was performed by a conventional method using "DNA Thermal Cycler" manufactured by Life Technologies Corporation and using KOD FX Neo (manufactured by Toyobo Co., Ltd.) as a reaction reagent.

Primers for Amplifying Hph Gene

```
                                                (SEQ ID NO: 9)
(a-2) 5'-ATACTCGAGGAGATGACGTTGGAGGGGCAAGGTCG-3'

(SEQ ID NO: 10)
(b-2) 5'-ATACGCGTCTATTCCTTTGCCCTCGGACGAGTGCT-3'
```

The primer (a-2) has an XhoI restriction enzyme site added thereto, and the primer (b-2) has an MluI restriction enzyme site added thereto.

The reaction liquid produced by each PCR described above was subjected to electrophoresis using 1% agarose gel. As a result, when the genomic DNA of the TH-1 strain was used as a template, an about 0.5-kbp DNA fragment corresponding to the rpsL gene was detected, and when the pJR225 plasmid DNA was used as a template, an about 1.0-kbp DNA fragment corresponding to the hph gene was detected.

The thus prepared DNA fragment containing the rpsL gene and DNA fragment containing the hph gene were cleaved with a restriction enzyme SalI and a restriction enzyme XhoI, respectively, and were mixed with an *Escherichia coli* plasmid vector pUC19 (GenBank:

M77789.2) that had been cleaved with a restriction enzyme SmaI, followed by ligation to each other using T4 DNA Ligase (manufactured by Takara Bio Inc.).

*Escherichia coli* JM109 was transformed with the resultant ligation solution by a calcium chloride method, and the transformant was applied to LB agar medium containing 50 μg/mL of ampicillin and 50 μg/mL of hygromycin. The grown strain on the medium was subjected to liquid culture by a conventional method, the plasmid DNA was extracted from the culture liquid, and the plasmid was cleaved with a restriction enzyme MluI. Thus, the inserted fragments were identified. As a result, in addition to the about 2.7-kbp DNA fragment of the pUC19 vector, an about 1.5-kbp DNA fragment corresponding to the sequence of the rpsL gene and the hph gene linked to each other was found.

The constructed plasmid containing a marker cassette in which the rpsL gene and the hph gene were linked to each other was named pUC-Sm$^s$•Hm$^r$.

(3) Construction of Mutant ilvH Gene [ilvH(G14D)]

Through use of the genomic DNA of the wild strain of the TH-1 strain extracted in (2-1) as a template, DNA fragments respectively containing a 5'-side region and a 3'-side region of a mutant ilvH gene [ilvH(G14D)] were each amplified by a PCR method. The following primers were used for the PCR. The primers contain sequences corresponding to a G14D mutation, and hence when the regions of the ilvH gene are amplified with these primers, DNA regions of the mutant ilvH gene [ilvH(G14D)] having the G14D mutation introduced thereinto can be amplified. The PCR was performed by a conventional method using "DNA Thermal Cycler" manufactured by Life Technologies Corporation and using KOD FX Neo (manufactured by Toyobo Co., Ltd.) as a reaction reagent.

Primers for amplifying 5'-side region of ilvH(G14D) gene

```
                                           (SEQ ID NO: 11)
(a-3) 5'-ATGAATTCCCCGGAAGCGACAAGCAGTTCCTGGGG-3'

(SEQ ID NO: 12)
(b-3) 5'-ACAACGCGTCCGATTCGTTTTCCACCAGCAGTGCA-3'
```

The primer (a-3) has an EcoRI restriction enzyme site added thereto, and the primer (b-3) has an MluI restriction enzyme site added thereto. The 9th nucleotide from the 5' end of SEQ ID NO: 12 of (b-3) is the mutation site.

Primers for amplifying 3'-side region of ilvH(G14D) gene

```
                                           (SEQ ID NO: 13)
(a-4) 5'-CGGACGCGTTGTCGCGCATCGCCGGGCTCTTTTCG-3'

(SEQ ID NO: 14)
(b-4) 5'-TTCTGCAGGCGCTTTGCCGCTTTGGTCCTGATGCA-3'
```

The primer (a-4) has an MluI restriction enzyme site added thereto, and the primer (b-4) has a PstI restriction enzyme site added thereto. The 4th nucleotide from the 5' end of SEQ ID NO: 13 of (a-4) is the mutation site.

The reaction liquid produced by each PCR described above was subjected to electrophoresis using 1% agarose gel. As a result, about 1.0-kbp DNA fragments corresponding to the 5'-side region and the 3'-side region of the ilvH(G14D) gene were respectively detected.

The thus prepared DNA fragment of the 5'-side region of the ilvH(G14D) gene was cleaved with restriction enzymes EcoRI and MluI, and the thus prepared DNA fragment of the 3'-side region of the mutant ilvH(G14D) gene was cleaved with restriction enzymes MluI and PstI. The cleaved products were mixed with a pUC19 vector that had been cleaved with restriction enzymes EcoRI and PstI, followed by ligation to each other using T4 DNA Ligase (manufactured by Takara Bio Inc.).

*Escherichia coli* JM109 was transformed with the resultant ligation solution by a calcium chloride method, and the transformant was applied to LB agar medium containing 50 μg/mL of ampicillin. The grown strain on the medium was subjected to liquid culture by a conventional method, the plasmid DNA was extracted from the culture liquid, and the plasmid was cleaved with restriction enzymes EcoRI and PstI. Thus, the inserted fragments were identified. As a result, in addition to the about 2.7-kbp DNA fragment of the pUC19 vector, an about 2.0-kbp DNA fragment corresponding to the sequence of the 5'-side region and the 3'-side region of the ilvH(G14D) gene linked to each other was found.

In this plasmid, the 5'-side region and the 3'-side region of the ilvH(G14D) gene are linked to each other, and ilvH (G14D) is cloned as one complete gene. The constructed plasmid containing the ilvH(G14D) gene was named pUC-ilvH(G14D).

(4) Construction of Plasmid for Labeling ilvH

The pUC-Sm$^s$•Hm$^r$ prepared in (2) above was cleaved with the restriction enzyme MluI, and subjected to electrophoresis using 1% agarose gel. After that, the about 1.5-kbp DNA fragment of the marker cassette in which the rpsL gene and the hph gene were linked to each other was excised from the agarose gel, and the gel was frozen and thawed. Thus, the DNA was recovered from the gel.

The recovered DNA fragment of the marker cassette was mixed with pUC-ilvH(G14D) generated in (3), which had been cleaved with the restriction enzyme MluI, followed by ligation to each other using T4 DNA Ligase (manufactured by Takara Bio Inc.).

*Escherichia coli* JM109 was transformed with the resultant ligation solution by a calcium chloride method, and the transformant was applied to LB agar medium containing 50 μg/mL of ampicillin and 50 μg/mL of hygromycin. The grown strain on the medium was subjected to liquid culture by a conventional method, the plasmid DNA was extracted from the culture liquid, and the plasmid was cleaved with the restriction enzyme MluI. Thus, the inserted fragments were identified. As a result, in addition to the about 4.7-kbp DNA fragment of the pUC-ilvH(G14D) plasmid, an about 1.5-kbp DNA fragment corresponding to the sequence of the marker cassette was found.

The constructed plasmid for labeling ilvH was named pUC-ilvH(G14D)-Sm$^s$•Hm$^r$.

(5) Introduction of G14D Mutation into ilvH Gene of TH-1 Strain (5-1) Labeling of ilvH Gene with Marker Cassette (Positive Selection)

The circular plasmid pUC-ilvH(G14D)-Sm$^s$•Hm$^r$ prepared in (4) was linearized by being cleaved with restriction enzymes EcoRI and PstI. With the resultant linear pUC-ilvH(G14D)-Sm$^s$•Hm$^r$, the NOC269 strain, which was the streptomycin-resistant strain of the TH-1 strain acquired in (1), was transformed by an electric pulse method (electroporation method). The transformant was applied to A-solid medium containing 100 μg/mL of hygromycin, and was cultured in a chamber filled with a mixed gas of $H_2:O_2:CO_2=7.5:1:1.5$ at 50° C. for 60 hours.

Each of the grown strains on the A-solid medium was restreaked onto A-solid medium containing 100 μg/mL of hygromycin or 500 µg/mL of streptomycin, and was cultured in a chamber filled with a mixed gas of $H_2:O_2:CO_2=7.5:1:1.5$ at 50° C. for 60 hours.

Through use of a hygromycin-resistant and streptomycin-sensitive strain obtained as a result of the foregoing as a template, a DNA region containing the ilvH gene was amplified by a colony PCR method. The following primers were used for the PCR. The primers are the combination of the primers (a-3) and (b-4) used in (3), and amplify an about 2.0-kbp DNA region containing the ilvH gene through PCR using the genomic DNA of the wild-type TH-1 strain as a template. The PCR was performed by a conventional method using "DNA Thermal Cycler" manufactured by Life Technologies Corporation and using TaKaRa Ex Taq (manufactured by Takara Bio Inc.) as a reaction reagent.

Primers for Amplifying Region Containing ilvH Gene

```
                                              (SEQ ID NO: 11)
(a-3) 5'-ATGAATTCCCCGGAAGCGACAAGCAGTTCCTGGGG-3'

(SEQ ID NO: 14)
(b-4) 5'-TTCTGCAGGCGCTTTGCCGCTTTGGTCCTGATGCA-3'
```

The produced reaction liquid was subjected to electrophoresis using 1% agarose gel. As a result, an about 3.5-kbp DNA fragment corresponding to a sequence having the marker cassette inserted into ilvH was detected. A strain in which the marker cassette was inserted into the ilvH gene, that is, the ilvH gene was labeled with the marker was named NOC278 strain.

(5-2) Substitution of ilvH Gene by ilvH(G14D) Gene (Counterselection)

The circular plasmid pUC-ilvH(G14D) prepared in (3) was linearized by being cleaved with restriction enzymes EcoRI and PstI. The NOC278 strain, which was the ilvH gene-labeled strain acquired in (5-1), was transformed with the resultant linear pUC-ilvH(G14D) by an electric pulse method (electroporation method). The transformant was applied to A-solid medium containing 500 µg/mL of streptomycin, and was cultured in a chamber filled with a mixed gas of $H_2:O_2:CO_2=7.5:1:1.5$ at 50° C. for 60 hours.

Each of the grown strains on the A-solid medium was restreaked onto A-solid medium containing 100 µg/mL of hygromycin or 500 µg/mL of streptomycin, and was cultured in a chamber filled with a mixed gas of $H_2:O_2:CO_2=7.5:1:1.5$ at 50° C. for 60 hours.

Through use of the hygromycin-sensitive and streptomycin-resistant strain obtained as a result of the foregoing as a template, a DNA region containing the ilvH gene was amplified by a colony PCR method. The colony PCR was performed by the same method as in (5-1).

The produced reaction liquid was subjected to electrophoresis using 1% agarose gel. As a result, the same about 2.0-kbp DNA fragment as that in the case of performing PCR using the genomic DNA of the wild-type TH-1 strain as a template was detected. That is, this corresponds to a sequence from which the marker cassette has been removed.

The amplified about 2.0-kbp DNA fragment was cleaved with the restriction enzyme MluI and subjected to electrophoresis using 1% agarose gel, and as a result, two about 1.0-kbp DNA fragments to be produced in the case of cleavage at the MluI site introduced together with the G14D mutation in (3) were detected. The about 2.0-kbp DNA fragment to be amplified in the case of using the genomic DNA of the wild-type TH-1 strain as a template does not contain any MluI site, and hence, even when subjected to a reaction with the restriction enzyme MluI, is not cleaved and keeps the 2.0-kbp size. Accordingly, a strain for which two about 1.0-kbp DNA fragments are detected through cleavage with MluI is a strain in which the ilvH gene has been substituted with the ilvH(G14D) gene, that is, the G14D mutation has been introduced into the ilvH gene. The strain having the G14D mutation in the ilvH gene was named NOC279 strain.

(6) Verification of Desensitization to Feedback Inhibition by Valine

The NOC279 strain, which was a strain having the G14D mutation in the wild-type ilvH gene of the *Hydrogenophilus* bacterium, was inoculated into each of test tubes having placed therein 5 mL of A-liquid medium containing 1 mM or 10 mM valine using a platinum loop, the test tube was filled with a mixed gas of $H_2:O_2:CO_2=7.5:1:1.5$, and shaking culture was performed at 50° C.

The wild-type *Hydrogenophilus* bacterium is inhibited from growth in the presence of 1 mM valine, but the NOC279 strain having the G14D mutation introduced into the gene encoding acetolactate synthase III was not inhibited from growth even in the presence of 10 mM valine. Thus, the NOC279 strain is desensitized to feedback inhibition by valine.

(7) Valine Production

The NOC279 strain, which was a strain having the G14D mutation in the ilvH gene of *Hydrogenophilus thermoluteolus*, was inoculated into A-liquid medium using a platinum loop, and was subjected to shaking culture at 50° C. for 30 hours with a mixed gas of $H_2:O_2:CO_2=7.5:1:1.5$ being supplied along with the culture.

After the culture, valine in the culture supernatant obtained by centrifugation (4° C., 15,000 rpm, 1 minute) was quantified, and as a result, it was found that valine was produced at 9 mM in the medium supernatant. When the wild-type *Hydrogenophilus thermoluteolus* TH-1 strain was similarly cultured, and valine in the culture supernatant was quantified, the result was 0.1 mM or less.

(8) Deposited Strains

*Hydrogenophilus thermoluteolus* NOC279 strain was deposited to NITE Patent Microorganisms Depositary, National Institute of Technology and Evaluation (2-5-8 Kazusakamatari, Kisarazu-shi, Chiba, Japan (postal code 292-0818)). For *Hydrogenophilus thermoluteolus* NOC279 strain, the accession number is BP-02829 and the date of acceptance is Nov. 22, 2018. Accordingly, this strain is available to the public.

Furthermore, all strains described in the present specification are internationally deposited under the Budapest Treaty, or are possessed by organizations that furnish the strains without any terms or conditions, or are marketed, or can be obtained by anyone by following some procedures, and therefore, these strains are all available to the general public.

INDUSTRIAL APPLICABILITY

The recombinant of the present invention effectively produces valine using carbon dioxide as a sole carbon source, and therefore, it is able to efficiently produce valine which can be utilized in drug, food, cosmetics, animal feed additives, and the like while solving global warming caused by increased emissions of carbon dioxide.

The invention claimed is:

1. A mutant acetolactate synthase III small subunit gene comprising a first mutant base sequence including SEQ ID NO: 2 in which at least one mutation selected from the group consisting of the following (i) to (p) is present in SEQ ID NO: 2
   (i) a substitution of AAC at base Nos. 31 to 33 with GAT, GAC, CAT, CAC, GCT, GCC, GCA, or GCG;
   (j) a substitution of GGC at base Nos. 40 to 42 with GAT, GAC, GCT, GCC, GCA, or GCG;
   (k) a substitution of TCG at base Nos. 49 to 51 with TTT or TTC;
   (l) a substitution of AAC at base Nos. 85 to 87 with AAA, AAG, TAT, TAC, GAT, GAC, CAT, or CAC;
   (m) a substitution of ACC at base Nos. 100 to 102 with ATT, ATC, or ATA;
   (n) a substitution of GCA at base Nos. 106 to 108 with GTT, GTC, GTA, or GTG;
   (o) a substitution of CGC at base Nos. 250 to 252 with TAA, TAG, or TGA; and
   (p) a substitution of CTC at base Nos. 391 to 393 with CGT, CGC, CGA, CGG, AGA, or AGG; or
   a second mutation base sequence having 90% or more identity to the first mutant base sequence, provided that said at least one mutation is present in the second mutant base sequence.

2. A *Hydrogenophilus* bacterium, including the mutant acetolactate synthase III small subunit gene according to claim 1.

3. A method of producing valine, including a step of culturing the *Hydrogenophilus* bacterium according to claim 2 through use of carbon dioxide as a substantially sole carbon source.

4. The mutant acetolactate synthase III small subunit gene according to claim 1, wherein the mutant acetolactate synthase III small subunit gene comprises the gene formed of a mutant base sequence having the mutation of the substitution of AAC at base Nos. 31 to 33 with GAT, GAC, CAT, CAC, GCT, GCC, GCA, or GCG in a base sequence set forth in SEQ ID NO: 2.

5. The mutant acetolactate synthase III small subunit gene according to claim 1, wherein the mutant acetolactate synthase III small subunit gene comprises the gene formed of a mutant base sequence having the mutation of the substitution GGC at base Nos. 40 to 42 with GAT, GAC, GCT, GCC, GCA, or GCG in a base sequence set forth in SEQ ID NO: 2.

6. The mutant acetolactate synthase III small subunit gene according to claim 1, wherein the mutant acetolactate synthase III small subunit gene comprises the gene formed of a mutant base sequence having the mutation of the substitution of TCG at base Nos. 49 to 51 with TTT or TTC in a base sequence set forth in SEQ ID NO: 2.

7. The mutant acetolactate synthase III small subunit gene according to claim 1, wherein the mutant acetolactate synthase III small subunit gene comprises the gene formed of a mutant base sequence having the mutation of the substitution of of AAC at base Nos. 85 to 87 with AAA, AAG, TAT, TAC, GAT, GAC, CAT, or CAC in a base sequence set forth in SEQ ID NO: 2.

8. The mutant acetolactate synthase III small subunit gene according to claim 1, wherein the mutant acetolactate synthase III small subunit gene comprises the gene formed of a mutant base sequence having the mutation of the substitution of ACC at base Nos. 100 to 102 with ATT, ATC, or ATA in a base sequence set forth in SEQ ID NO: 2.

9. The mutant acetolactate synthase III small subunit gene according to claim 1, wherein the mutant acetolactate synthase III small subunit gene comprises the gene formed of a mutant base sequence having the mutation of the substitution of GCA at base Nos. 106 to 108 with GTT, GTC, GTA, or GTG in a base sequence set forth in SEQ ID NO: 2.

10. The mutant acetolactate synthase III small subunit gene according to claim 1, wherein the mutant acetolactate synthase III small subunit gene comprises the gene formed of a mutant base sequence having the mutation of the substitution of CGC at base Nos. 250 to 252 with TAA, TAG, or TGA in a base sequence set forth in SEQ ID NO: 2.

11. The mutant acetolactate synthase III small subunit gene according to claim 1, wherein the mutant acetolactate synthase III small subunit gene comprises the gene formed of a mutant base sequence having the mutation of the substitution of CTC at base Nos. 391 to 393 with CGT, CGC, CGA, CGG, AGA, or AGG in a base sequence set forth in SEQ ID NO: 2.

12. The mutant acetolactate synthase III small subunit gene according to claim 1, wherein the mutant acetolactate synthase III small subunit gene comprises the gene formed of a mutant base sequence having the mutation of the substitution of AAC at base Nos. 40 to 42 with GAT in a base sequence set forth in SEQ ID NO: 2.

13. The mutant acetolactate synthase III small subunit gene according to claim 1, wherein the mutant acetolactate synthase III small subunit gene comprises the gene formed of a mutant base sequence having the mutation of the substitution of AAC at base Nos. 40 to 42 with GAC in a base sequence set forth in SEQ ID NO: 2.

14. The mutant acetolactate synthase III small subunit gene according to claim 1, wherein the mutant acetolactate synthase III small subunit gene comprises the gene formed of a mutant base sequence having the mutation of the substitution of AAC at base Nos. 31 to 33 with GAT in a base sequence set forth in SEQ ID NO: 2.

15. The mutant acetolactate synthase III small subunit gene according to claim 1, wherein the mutant acetolactate synthase III small subunit gene comprises the gene formed of a mutant base sequence having the mutation of the substitution of AAC at base Nos. 31 to 33 with GAC in a base sequence set forth in SEQ ID NO: 2.

* * * * *

SEQUENCE LISTING

<160> NUMBER OF SEQ ID NOS: 14

<210> SEQ ID NO 1
<211> LENGTH: 163
<212> TYPE: PRT
<213> ORGANISM: Hydrogenophilus thermoluteolus

<400> SEQUENCE: 1

```
Met Arg His Val Ile Ala Leu Leu Val Glu Asn Glu Ser Gly Ala Leu
1               5                   10                  15

Ser Arg Ile Ala Gly Leu Phe Ser Ala Arg Gly Tyr Asn Ile Glu Ser
            20                  25                  30

Leu Thr Val Ala Pro Thr Glu Asp Glu Ser Leu Ser Arg Met Thr Ile
        35                  40                  45

Val Thr Thr Gly Ser Asp Asp Val Ile Glu Gln Ile Thr Lys Gln Leu
    50                  55                  60

Asn Lys Leu Ile Asp Thr Val Lys Val Val Asp Leu Ser Glu Ser Ala
65                  70                  75                  80

His Ile Glu Arg Glu Leu Met Met Val Lys Val Arg Ala Val Gly Ser
                85                  90                  95

Asp Arg Glu Glu Leu Lys Arg Leu Ala Asp Ile Phe Arg Ala Arg Ile
            100                 105                 110

Ile Asp Val Thr Asp Thr Thr Tyr Val Ile Glu Leu Thr Gly Asn Gln
        115                 120                 125

Gln Lys Leu Asn Ala Phe Leu Ala Ala Ile Ser Pro Ser Leu Ile Leu
    130                 135                 140

Glu Thr Val Arg Ser Gly Val Cys Gly Ile Ala Arg Gly Glu Arg Met
145                 150                 155                 160

Leu Lys Ala
```

<210> SEQ ID NO 2
<211> LENGTH: 492
<212> TYPE: DNA
<213> ORGANISM: Hydrogenophilus thermoluteolus

<400> SEQUENCE: 2

```
atgagacacg tgattgcact gctggtggaa aacgaatcgg gcgcgttgtc gcgcatcgcc    60
gggctctttt cggcgcgtgg ctacaacatc gaatcgctca ccgtcgcacc gaccgaagac   120
gagagcctgt cgcggatgac gatcgtcacc accggttcgg acgacgtgat cgaacagatc   180
accaagcagc tcaacaaact gatcgatacg gtcaaagtgg tcgacctctc cgaatccgcg   240
cacatcgagc gcgaactgat gatggtgaag gtccgtgccg tgggatcaga ccgcgaagag   300
ctcaaacgcc tggccgacat cttccgcgcc cggatcatcg acgtcaccga caccacctac   360
gtgatcgaac tcaccggcaa ccagcagaag ctcaacgcgt ttctggcggc gatctcgccc   420
agtctcatct tggagacggt gcgtagcggc gtctgcggca ttgcccgtgg cgagcgtatg   480
ttgaaagcct ga                                                      492
```

<210> SEQ ID NO 3
<211> LENGTH: 396
<212> TYPE: DNA
<213> ORGANISM: Hydrogenophilus thermoluteolus

<400> SEQUENCE: 3

```
atgccaacca tcaaccagtt ggtgcgtcgt ccgcggaaaa cggcgcccga aaagagcaaa    60
gtgccggcgt tgcagggatg tccgcaaaaa cgaggcgtgt gtacgcgcgt ctataccacg   120
```

```
acgccgaaaa agccgaactc ggcccttcgt aaggtcgcga aagtgcgttt gaccaacggt      180
tacgaggtga tttcgtacat cggcggcgaa gggcacaatc tgcaagaaca ctcggtggtg      240
ctgattcgtg gcggccgggt gaaagacctg ccgggtgtgc gttaccacat cgtgcgcggt      300
tcgctcgact gcaaggggt caaggaccgt aagcaagggc gttccaagta cggggcgaag       360
cgtccgaagc cgggcgccgc tgcgggcaag aaataa                               396
```

```
<210> SEQ ID NO 4
<211> LENGTH: 1026
<212> TYPE: DNA
<213> ORGANISM: Escherichia coli

<400> SEQUENCE: 4
atgaaaaagc ctgaactcac cgcgacatct gtcgagaagt ttctgatcga aaagttcgac      60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat     180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat     360
gcgatcgctg cggccgatct tagccagacg agcgggttcg cccattcgg accgcaagga     420 atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600
tccaacaatg tcctgacgga caatggccgc ataacagcgg tcattgactg agcgaggcg     660 atgttcgggg attcccaata cgaggtcgcc aacatcttct tctggaggcc gtggttggct     720
tgtatggagc agcagacgcg ctacttcgag cggaggcatc cggagcttgc aggatcgccg     780
cggctccggg cgtatatgct ccgcattggt cttgaccaac tctatcagag cttggttgac     840
ggcaatttcg atgatgcagc ttgggcgcag ggtcgatgcg acgcaatcgt ccgatccgga     900
gccgggactg tcgggcgtac acaaatcgcc cgcagaagcg cggccgtctg gaccgatggc     960
tgtgtagaag tactcgccga tagtggaaac cgacgcccca gcactcgtcc gagggcaaag    1020
gaatag                                                              1026
```

```
<210> SEQ ID NO 5
<211> LENGTH: 795
<212> TYPE: DNA
<213> ORGANISM: Escherichia coli

<400> SEQUENCE: 5
atgattgaac aagatggatt gcacgcaggt tctccggccg cttgggtgga gaggctattc       60
ggctatgact gggcacaaca gacaatcggc tgctctgatg ccgccgtgtt ccggctgtca     120 gcgcagggc gcccggttct ttttgtcaag accgacctgt ccggtgccct gaatgaactc      180
caagacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa    480
```

```
gagcatcagg ggctcgcgcc agccgaactg ttcgccaggc tcaaggcgcg gatgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795
```

```
<210> SEQ ID NO 6
<211> LENGTH: 762
<212> TYPE: DNA
<213> ORGANISM: Staphylococcus aureus

<400> SEQUENCE: 6
atgaatggac caataataat gactagagaa gaaagaatga agattgttca tgaaattaag     60
gaacgaatat tggataaata tggggatgat gttaaggcta ttggtgttta tggctctctt    120
ggtcgtcaga ctgatgggcc ctattcggat attgagatga tgtgtgtcat gtcaacagag    180
gaagcagagt tcagccatga atggacaacc ggtgagtgga aggtggaagt gaattttgat    240
agcgaagaga ttctactaga ttatgcatct caggtggaat cagattggcc gcttacacat    300
ggtcaatttt tctctatttt gccgatttat gattcaggtg gatacttaga gaaagtgtat    360
caaactgcta atcggtagaa gcccaaacg ttccacgatg cgatttgtgc ccttatcgta    420
gaagagctgt ttgaatatgc aggcaaatgg cgtaatattc gtgtgcaagg accgacaaca    480
tttctaccat ccttgactgt acaggtagca atggcaggtg ccatgttgat tggtctgcat    540
catcgcatct gttatacgac gagcgcttcg gtcttaactg aagcagttaa gcaatcagat    600
cttccttcag ttatgaccta ctgtgccag ttcgtaatgt ctggtcaact ttccgactct    660
gagaaacttc tggaatcgct agagaatttc tggaatggga ttcaggagtg gacagaacga    720
cacggatata tagtggatgt gtcaaaacgc ataccatttt ga                       762
```

```
<210> SEQ ID NO 7
<211> LENGTH: 35
<212> TYPE: DNA
<213> ORGANISM: Artificial sequence
<220> FEATURE:
<223> OTHER INFORMATION: PCR primer

<400> SEQUENCE: 7
atacgcgtcc tccgatgcgt cgtaagggaa acgtc                                35
```

```
<210> SEQ ID NO 8
<211> LENGTH: 35
<212> TYPE: DNA
<213> ORGANISM: Artificial sequence
<220> FEATURE:
<223> OTHER INFORMATION: PCR primer

<400> SEQUENCE: 8
atagtcgact tatttcttgc ccgcagcggc gcccg                                35
```

```
<210> SEQ ID NO 9
<211> LENGTH: 35
<212> TYPE: DNA
<213> ORGANISM: Artificial sequence
<220> FEATURE:
<223> OTHER INFORMATION: PCR primer

<400> SEQUENCE: 9
```
atactcgagg agatgacgtt ggaggggcaa ggtcg                    35

<210> SEQ ID NO 10
<211> LENGTH: 35
<212> TYPE: DNA
<213> ORGANISM: Artificial sequence
<220> FEATURE:
<223> OTHER INFORMATION: PCR primer

<400> SEQUENCE: 10
atacgcgtct attcctttgc cctcggacga gtgct                    35

<210> SEQ ID NO 11
<211> LENGTH: 35
<212> TYPE: DNA
<213> ORGANISM: Artificial sequence
<220> FEATURE:
<223> OTHER INFORMATION: PCR primer

<400> SEQUENCE: 11
atgaattccc cggaagcgac aagcagttcc tgggg                    35

<210> SEQ ID NO 12
<211> LENGTH: 35
<212> TYPE: DNA
<213> ORGANISM: Artificial sequence
<220> FEATURE:
<223> OTHER INFORMATION: PCR primer

<400> SEQUENCE: 12
acaacgcgtc cgattcgttt tccaccagca gtgca                    35

<210> SEQ ID NO 13
<211> LENGTH: 35
<212> TYPE: DNA
<213> ORGANISM: Artificial sequence
<220> FEATURE:
<223> OTHER INFORMATION: PCR primer

<400> SEQUENCE: 13
cggacgcgtt gtcgcgcatc gccgggctct tttcg                    35

<210> SEQ ID NO 14
<211> LENGTH: 35
<212> TYPE: DNA
<213> ORGANISM: Artificial sequence
<220> FEATURE:
<223> OTHER INFORMATION: PCR primer

<400> SEQUENCE: 14
ttctgcaggc gctttgccgc tttggtcctg atgca                    35